US012023491B2

(12) United States Patent
Kern et al.

(10) Patent No.: US 12,023,491 B2
(45) Date of Patent: Jul. 2, 2024

(54) MODULATED WAVEFORM TREATMENT DEVICE AND METHOD

(71) Applicant: NSE Products, Inc., Provo, UT (US)

(72) Inventors: Dale G. Kern, Hyde Park, UT (US); DucToan Thanh Doan, Orem, UT (US)

(73) Assignee: NSE Products, Inc., Provo, UT (US)

( * ) Notice: Subject to any disclaimer, the term of this patent is extended or adjusted under 35 U.S.C. 154(b) by 203 days.

(21) Appl. No.: 17/221,415

(22) Filed: Apr. 2, 2021

(65) Prior Publication Data

US 2021/0308452 A1  Oct. 7, 2021

Related U.S. Application Data

(60) Provisional application No. 63/004,839, filed on Apr. 3, 2020.

(51) Int. Cl.
*A61N 1/32* (2006.01)
*A61N 1/36* (2006.01)
(Continued)

(52) U.S. Cl.
CPC .......... *A61N 1/328* (2013.01); *A61N 5/0616* (2013.01); *A61N 2005/0659* (2013.01); *A61N 5/067* (2021.08)

(58) Field of Classification Search
CPC .............. A61N 1/328; A61N 1/36034; A61N 2005/0659; A61N 5/0616; A61N 5/067
(Continued)

(56) References Cited

U.S. PATENT DOCUMENTS

| 1,913,462 A | 6/1933 | Edward |
| 2,480,023 A | 8/1949 | Holden |

(Continued)

FOREIGN PATENT DOCUMENTS

| DE | 1757913 A1 | 6/1971 |
| DE | 20103026 U1 | 8/2001 |

(Continued)

OTHER PUBLICATIONS

Partial Search Report dated Jul. 14, 2021 in connection with International Patent Application No. PCT/US2021/025579, 8 pages.
(Continued)

*Primary Examiner* — Jonathan T Kuo
*Assistant Examiner* — Vynn V Huh
(74) *Attorney, Agent, or Firm* — Dorsey & Whitney LLP

(57) ABSTRACT

A microcurrent treatment device has one or more electrodes or emitters configured for electrical communication with the surface of a subject's skin. A voltage or current supply is adapted to generate an electrical waveform or other energetic waveform for application to the skin surface, via the one or more electrodes or emitters, and a controller is configured to modulate the waveform. The controller can modulate consecutive pulses of the waveform so that the pulse width, period, frequency, amplitude or integrated amplitude of the consecutive pulses varies in a predefined, random, pseudorandom, or other aperiodic manner, or so that the pulses exhibit a degree of statistical randomness, over a predefined period. The period can cover a set of consecutive pulses defining a treatment cycle, or a continuous subset of consecutive pulses defining one or more phases of a treatment cycle.

27 Claims, 21 Drawing Sheets

(51) Int. Cl.
*A61N 1/40* (2006.01)
*A61N 5/06* (2006.01)
*A61N 5/067* (2006.01)
*A61N 7/00* (2006.01)

(58) Field of Classification Search
USPC .......... 607/1–95, 115–156, 88–94; 606/2–19
See application file for complete search history.

(56) References Cited

U.S. PATENT DOCUMENTS

| | | | |
|---|---|---|---|
| 2,682,675 A | 7/1954 | Frank | |
| 2,764,773 A | 10/1956 | Roy et al. | |
| 3,234,933 A | 2/1966 | Martin | |
| 3,320,947 A | 5/1967 | Hans | |
| 3,906,940 A | 9/1975 | Kawada | |
| 3,968,789 A | 7/1976 | Simoncini | |
| 4,027,348 A | 6/1977 | Flowers et al. | |
| 4,033,356 A | 7/1977 | Hara | |
| 4,249,521 A | 2/1981 | Gueret | |
| D262,672 S | 1/1982 | Iten et al. | |
| 4,343,265 A | 8/1982 | Belschner | |
| 4,463,485 A | 8/1984 | Gueret | |
| D285,131 S | 8/1986 | Wilkeson | |
| 4,846,181 A | 7/1989 | Miller | |
| 4,907,601 A | 3/1990 | Frick | |
| 5,016,616 A | 5/1991 | Hu | |
| D321,434 S | 11/1991 | Strickler | |
| 5,147,297 A | 9/1992 | Myers et al. | |
| 5,162,043 A | 11/1992 | Lew et al. | |
| 5,176,130 A | 1/1993 | Kim | |
| D333,730 S | 3/1993 | Martin | |
| D333,922 S | 3/1993 | Strickler et al. | |
| 5,228,165 A | 7/1993 | Westberry et al. | |
| D342,319 S | 12/1993 | Cheng | |
| D344,137 S | 2/1994 | Yoo | |
| 5,298,017 A | 3/1994 | Theeuwes et al. | |
| 5,326,341 A | 7/1994 | Lew et al. | |
| D351,947 S | 11/1994 | Fitzgerald | |
| D357,322 S | 4/1995 | Matthews | |
| 5,405,317 A | 4/1995 | Myers et al. | |
| D358,654 S | 5/1995 | Smith | |
| 5,441,613 A | 8/1995 | Mccormick et al. | |
| D368,343 S | 3/1996 | Gebhard et al. | |
| D369,220 S | 4/1996 | Huang | |
| D369,447 S | 4/1996 | Kubes et al. | |
| D370,124 S | 5/1996 | Chamieh | |
| 5,514,167 A | 5/1996 | Smith et al. | |
| 5,667,487 A | 9/1997 | Henley | |
| D385,351 S | 10/1997 | Manzie et al. | |
| 5,685,837 A | 11/1997 | Horstmann | |
| D409,337 S | 5/1999 | Johnson | |
| D414,582 S | 9/1999 | Hwang | |
| 6,076,222 A | 6/2000 | Jolly | |
| 6,119,038 A | 9/2000 | Cook | |
| 6,266,560 B1 | 7/2001 | Zhang et al. | |
| 6,267,736 B1 | 7/2001 | Mccambridge et al. | |
| 6,347,246 B1 | 2/2002 | Perrault et al. | |
| D460,554 S | 7/2002 | Park | |
| 6,421,561 B1 | 7/2002 | Morris | |
| 6,424,862 B1 | 7/2002 | Brown et al. | |
| D462,483 S | 9/2002 | Campbell | |
| 6,443,915 B1 | 9/2002 | Hwang | |
| 6,452,584 B1 | 9/2002 | Walker et al. | |
| 6,584,349 B1 | 6/2003 | Sage, Jr. et al. | |
| 6,588,964 B1 | 7/2003 | Au et al. | |
| D479,336 S | 9/2003 | La et al. | |
| D481,463 S | 10/2003 | Cook et al. | |
| 6,653,014 B2 | 11/2003 | Anderson et al. | |
| D484,605 S | 12/2003 | Cook et al. | |
| D485,990 S | 2/2004 | Wallace | |
| D486,233 S | 2/2004 | Cook et al. | |
| D487,154 S | 2/2004 | Cook et al. | |
| 6,743,215 B2 | 6/2004 | Bernabei | |
| 6,766,199 B2 | 7/2004 | Cook et al. | |
| D496,731 S | 9/2004 | Park | |
| 6,801,808 B2 | 10/2004 | Lee | |
| 6,840,955 B2 | 1/2005 | Ein | |
| D514,328 S | 2/2006 | Huang | |
| D523,962 S | 6/2006 | Huang | |
| 7,194,316 B2 | 3/2007 | Bousfield et al. | |
| D539,916 S | 4/2007 | Baldacchini | |
| D539,917 S | 4/2007 | Park | |
| D544,092 S | 6/2007 | Lewis | |
| D545,970 S | 7/2007 | Eknoian et al. | |
| D545,971 S | 7/2007 | Eknoian et al. | |
| D546,958 S | 7/2007 | Kim | |
| D548,339 S | 8/2007 | Stonier et al. | |
| D555,407 S | 11/2007 | Lan | |
| 7,305,269 B2 | 12/2007 | Cook et al. | |
| 7,306,569 B2 | 12/2007 | LaJoie et al. | |
| 7,320,691 B2 | 1/2008 | Pilcher et al. | |
| D564,087 S | 3/2008 | Yodfat et al. | |
| D565,306 S | 4/2008 | Orgna et al. | |
| D567,387 S | 4/2008 | Nan | |
| D571,926 S | 6/2008 | Wu | |
| 7,383,083 B2 | 6/2008 | Fischer et al. | |
| 7,384,377 B2 | 6/2008 | Berman | |
| 7,386,347 B2 | 6/2008 | Lee et al. | |
| 7,386,906 B2 | 6/2008 | Roth et al. | |
| 7,395,110 B2 | 7/2008 | Hofmann et al. | |
| 7,415,306 B2 | 8/2008 | Levin et al. | |
| D589,257 S | 3/2009 | Van | |
| 7,786,626 B2 | 8/2010 | Reishus et al. | |
| D629,528 S | 12/2010 | Adkisson | |
| 7,850,997 B2 | 12/2010 | Romero et al. | |
| D636,886 S | 4/2011 | Lopez | |
| D636,933 S | 4/2011 | Newman | |
| 7,959,951 B2 | 6/2011 | Stefano et al. | |
| D646,795 S | 10/2011 | Seehoff et al. | |
| D649,258 S | 11/2011 | Lev-ran | |
| D661,811 S | 6/2012 | Ferguson et al. | |
| D664,665 S | 7/2012 | Wahng et al. | |
| 8,271,090 B1 | 9/2012 | Hartman et al. | |
| D671,281 S | 11/2012 | Singer | |
| 8,386,032 B2 | 2/2013 | Bachinski et al. | |
| D682,497 S | 5/2013 | Wargo et al. | |
| D685,084 S | 6/2013 | Guarraia et al. | |
| 8,523,791 B2 | 9/2013 | Castel | |
| 8,560,080 B2 | 10/2013 | Singal et al. | |
| D696,160 S | 12/2013 | Kittoe | |
| 8,639,361 B2 | 1/2014 | Nathanson | |
| D699,903 S | 2/2014 | Singer | |
| 8,679,039 B2 | 3/2014 | Tieu et al. | |
| 8,745,807 B2 | 6/2014 | Varner et al. | |
| D711,656 S | 8/2014 | Brewer et al. | |
| D715,553 S | 10/2014 | Brewer et al. | |
| D720,933 S | 1/2015 | Albers | |
| 8,945,104 B2 | 2/2015 | Boone et al. | |
| 8,954,155 B2 | 2/2015 | Campbell | |
| D726,418 S | 4/2015 | Gruber et al. | |
| 9,032,576 B2 | 5/2015 | Zelickson et al. | |
| D733,899 S | 7/2015 | Ferguson et al. | |
| D734,949 S | 7/2015 | Behnam | |
| 9,079,022 B2 | 7/2015 | Baird et al. | |
| 9,138,257 B2 | 9/2015 | Revivo | |
| D740,033 S | 10/2015 | Gruber et al. | |
| 9,205,254 B1 | 12/2015 | Britt et al. | |
| D749,325 S | 2/2016 | Middendorp | |
| D752,235 S | 3/2016 | Levi et al. | |
| 9,272,141 B2 | 3/2016 | Nichols | |
| D753,399 S | 4/2016 | Owen et al. | |
| D753,400 S | 4/2016 | Khoun et al. | |
| 9,301,657 B2 | 4/2016 | Miller et al. | |
| D768,391 S | 10/2016 | Kling et al. | |
| 9,474,898 B2 | 10/2016 | Gozani et al. | |
| D778,064 S | 2/2017 | Owen et al. | |
| D778,065 S | 2/2017 | Kern et al. | |
| D778,066 S | 2/2017 | Kern et al. | |
| D780,933 S | 3/2017 | Uchida et al. | |
| D781,588 S | 3/2017 | Lee | |
| D782,197 S | 3/2017 | Kern et al. | |
| D795,593 S | 8/2017 | Huang | |
| D796,212 S | 9/2017 | Thornton | |

(56) References Cited

U.S. PATENT DOCUMENTS

| | | |
|---|---|---|
| D797,461 S | 9/2017 | Dandridge et al. |
| D803,572 S | 11/2017 | Nichols |
| D810,312 S | 2/2018 | Cascini et al. |
| 10,046,160 B1 | 8/2018 | Kern |
| D828,570 S | 9/2018 | Boaz et al. |
| 10,080,428 B2 | 9/2018 | Kern |
| D829,445 S | 10/2018 | Kern et al. |
| D847,359 S | 4/2019 | Kern et al. |
| D863,574 S | 10/2019 | Yan et al. |
| 10,537,736 B2 | 1/2020 | Hyun et al. |
| 10,661,072 B2 | 5/2020 | Kern et al. |
| 10,765,199 B2 | 9/2020 | Kern |
| 10,772,473 B2 | 9/2020 | Johnstone et al. |
| D933,840 S | 10/2021 | Hermann et al. |
| 2002/0156402 A1 | 10/2002 | Woog et al. |
| 2002/0193831 A1 | 12/2002 | Smith |
| 2003/0004556 A1 | 1/2003 | Mcdaniel |
| 2003/0032900 A1 | 2/2003 | Ella |
| 2004/0220456 A1 | 11/2004 | Eppstein |
| 2004/0265395 A1 | 12/2004 | Sun et al. |
| 2005/0059914 A1 | 3/2005 | Kleinhenz et al. |
| 2005/0064528 A1 | 3/2005 | Kwon et al. |
| 2005/0113725 A1 | 5/2005 | Masuda |
| 2005/0142093 A1 | 6/2005 | Skover et al. |
| 2005/0197618 A1 | 9/2005 | Plummer et al. |
| 2005/0277950 A1 | 12/2005 | Pilcher et al. |
| 2005/0278877 A1 | 12/2005 | Akridge et al. |
| 2006/0010630 A1 | 1/2006 | Tse |
| 2006/0058714 A1 | 3/2006 | Rhoades |
| 2006/0276731 A1 | 12/2006 | Thiebaut et al. |
| 2007/0142845 A1 | 6/2007 | Akridge et al. |
| 2007/0179412 A1 | 8/2007 | Imboden et al. |
| 2007/0185431 A1 | 8/2007 | Kern |
| 2007/0276449 A1 | 11/2007 | Gunter et al. |
| 2008/0005860 A1 | 1/2008 | Niizaki et al. |
| 2008/0119913 A1 | 5/2008 | Powell et al. |
| 2008/0125682 A1 | 5/2008 | Bonneyrat |
| 2008/0167590 A1 | 7/2008 | Jon et al. |
| 2008/0222822 A1 | 9/2008 | Cobabe et al. |
| 2008/0295268 A1 | 12/2008 | Lei |
| 2008/0312579 A1 | 12/2008 | Chang et al. |
| 2009/0198159 A1 | 8/2009 | Linzell |
| 2009/0318853 A1 | 12/2009 | Reed et al. |
| 2010/0042018 A1 | 2/2010 | Kleinsinger |
| 2010/0049180 A1 | 2/2010 | Wells et al. |
| 2010/0217357 A1 | 8/2010 | Da et al. |
| 2010/0262051 A1 | 10/2010 | De |
| 2010/0292746 A1 | 11/2010 | Gorham |
| 2010/0305206 A9 | 12/2010 | Messadek |
| 2011/0015687 A1 | 1/2011 | Nebrigic et al. |
| 2011/0028548 A1 | 2/2011 | Fossel |
| 2011/0118655 A1 | 5/2011 | Fassih et al. |
| 2011/0184499 A1 | 7/2011 | Radi |
| 2011/0224743 A1 | 9/2011 | Britt |
| 2011/0230701 A1* | 9/2011 | Simon .................. A61N 1/0456 607/46 |
| 2011/0251537 A1 | 10/2011 | Yeo |
| 2012/0121313 A1 | 5/2012 | Thiebaut |
| 2012/0165708 A1 | 6/2012 | Parsloe |
| 2012/0165710 A1 | 6/2012 | Nichols |
| 2012/0209151 A1 | 8/2012 | Zhou et al. |
| 2013/0023805 A1 | 1/2013 | Ungemach et al. |
| 2013/0023806 A1 | 1/2013 | Ungemach et al. |
| 2013/0046212 A1 | 2/2013 | Nichols |
| 2013/0079689 A1 | 3/2013 | Thierman |
| 2013/0289416 A1 | 10/2013 | Feferberg |
| 2015/0034113 A1 | 2/2015 | Yamagishi et al. |
| 2015/0150754 A1 | 6/2015 | Kadra et al. |
| 2015/0265825 A1 | 9/2015 | Miller et al. |
| 2015/0305487 A1 | 10/2015 | Pardo et al. |
| 2015/0305969 A1 | 10/2015 | Giraud et al. |
| 2015/0359324 A1 | 12/2015 | Brewer |
| 2016/0045081 A1 | 2/2016 | Kern |
| 2016/0045678 A1 | 2/2016 | Vallero et al. |
| 2016/0183670 A1 | 6/2016 | Brewer et al. |
| 2016/0206087 A1 | 7/2016 | Skidmore et al. |
| 2016/0303364 A1 | 10/2016 | Osborne |
| 2017/0049278 A1 | 2/2017 | Thomassen |
| 2017/0073050 A1 | 3/2017 | Smith |
| 2017/0112333 A1 | 4/2017 | Mccauley |
| 2017/0189670 A1 | 7/2017 | Brunson et al. |
| 2018/0055720 A1 | 3/2018 | Sitkovetskiy et al. |
| 2018/0318585 A1 | 11/2018 | Pfeifer |
| 2018/0333574 A1 | 11/2018 | Pal |

FOREIGN PATENT DOCUMENTS

| | | | |
|---|---|---|---|
| GB | 1208149 A | 10/1970 | |
| JP | 2001293050 A | 10/2001 | |
| JP | 2004249061 A | 9/2004 | |
| JP | 2006061486 A | 3/2006 | |
| JP | 2010524625 A | 7/2010 | |
| JP | 2013106741 A | 6/2013 | |
| KR | 101068809 B1 | 10/2011 | |
| WO | 2004057999 A1 | 7/2004 | |
| WO | 2006019764 A2 | 2/2006 | |
| WO | 2008135953 A1 | 11/2008 | |
| WO | 2009136911 A1 | 11/2009 | |
| WO | 2013077284 A1 | 5/2013 | |
| WO | 2013132363 A1 | 9/2013 | |
| WO | 2013132364 A1 | 9/2013 | |
| WO | 2014024084 A1 | 2/2014 | |
| WO | 2014118596 A1 | 8/2014 | |
| WO | 2014145239 A1 | 9/2014 | |
| WO | 2014195516 A1 | 12/2014 | |
| WO | 2016025702 A1 | 2/2016 | |
| WO | 2016196635 A2 | 12/2016 | |
| WO | WO-2016196635 A2 * | 12/2016 | ......... A61N 1/36025 |
| WO | 2017027793 A1 | 2/2017 | |
| WO | 2018218183 A2 | 11/2018 | |
| WO | 2018218183 A3 | 1/2019 | |

OTHER PUBLICATIONS

W. Paulus, "Chapter 26 Transcranial Direct Current Stimulation (tDCS)" Clinical Neurophysiology Supplement, Jan. 1, 2003, vol. 56, pp. 249-254.

International Search Report and Written Opinion dated Sep. 6, 2021 for International Patent Application No. PCT/US2021/025579, 18 pages.

Foreo, "Face Scrub Brush & Anti Aging Skin Care", Face Scrub Brush & Anti Aging Skin Care | Luna TM by Foreo downloaded from <https://www.foreo.com/luna>, Jan. 21, 2016, 5.

International Search Report and Written Opinion dated Jan. 15, 2016 for International Patent Application No. PCT/US2015/045040, 22 pages.

International Preliminary Report on Patentability dated Nov. 24, 2016 for International Patent Application No. PCT/US2015/045040, 13 pages.

International Search Report and Written Opinion dated Nov. 26, 2018 for International Patent Application No. PCT/US2018/034714, 15 pages.

International Search Report and Written Opinion dated Dec. 1, 2016 for International Patent Application No. PCT/US2016/046738, 11 pages.

International Preliminary Report on Patentability dated Feb. 22, 2018 for International Patent Application No. PCT/US2016/046738, 8 pages.

"Facemaster Platinum Instruction Manual", downloaded from https://www.facemaster.com/pages/manual-and-quick-start-guides-for-facemaster-microcurrent-machine on Jan. 22, 2019, pp. 9.

"International Search Report and Written Opinion for PCT/US19/12219", mailed Apr. 19, 2019, 14 pages.

"Rejuvenique Facial Toning System #RJV10", from Salton, Inc., Aug. 8, 2001; 6 pages.

"TLV61220 Low-Input Voltage Step-Up Converter in Thin SOT-23 Package", Texas Instruments, May 2012, revised Dec. 2014, pp. 24.

Jung, Woo-Suk et al., "Powerful curved piezoelectric generator for wearable applications", Nano Energy, Science Direct, vol. 13, Apr. 2015, ISSN 2211-2855, pp. 174-181.

(56) References Cited

OTHER PUBLICATIONS

Moodie, "Clinique Advocates 'fitness for the face'", The Moodie Report, "Clinique advocates 'fitness for the face' with new Sculptwear range", downloaded from https://www.moodiereport.com/document.php?doc_id=43808, Sep. 6, 2015, 2.

Proactive, "Deep Cleansing Brush", Proactiv Advertisement—Deep Cleansing Brush, https://www1.proactiv.com, 1 page, date unknown.

Thakral, Gaurav et al., "Electrical stimulation to accelerate wound healing", Diabetic Foot & Ankle, 2013; 4:10.3402/dfa.v4i0.22081, Sep. 16, 2013, 1-9.

Xout, "X Out Wash In Treatement", X Out Wash In Treatment—Acne Treatment for Teens | X Out™, downloaded from https://www.xout.com/specialoffer/, Oct. 27, 2015, 1.

Office Action dated Oct. 17, 2023 in connection with European patent application No. 21721707.4, 6 pages.

\* cited by examiner

Summary of Statistical Analysis: Laser Doppler Flux

| Attribute | Treatment | Evaluation | N | Treatment Mean | Mean Difference From Baseline | Within-Treatment t-test p-value | Between-Treatment ANOVA p-value |
|---|---|---|---|---|---|---|---|
| Flux | Conductive Gel | Baseline | 25 | 227.04 | | | |
| | | Post Treatment | 25 | 166.55 | -60.49 | <0.0001* | 0.4512 |
| | MC Boost East | Baseline | 25 | 231.19 | | | |
| | | Post Treatment | 25 | 167.07 | -64.12 | <0.0001* | |

*Significant change from baseline

Summary of Statistical Analysis: Temperature

| Attribute | Treatment | Evaluation | N | Treatment Mean | Mean Difference From Baseline | Within-Treatment t-test p-value | Between-Treatment ANOVA p-value |
|---|---|---|---|---|---|---|---|
| Temperature | Conductive Gel | Baseline | 25 | 90.14 | | | |
| | | Post Treatment | 25 | 82.59 | -7.55 | <0.0001* | >0.5000 |
| | MC Boost East | Baseline | 25 | 90.24 | | | |
| | | Post Treatment | 25 | 82.73 | -7.50 | <0.0001* | |

*Significant change from baseline

Tolerability

| Subject # | Shave Cream/Razor | Setting 1 | Setting 2 | PRPWM |
|---|---|---|---|---|
| 1 | D | 1 sec tolerance | 1 sec tolerance | No discomfort after 30 second cycle |
| 2 | C1 | 3 sec tolerance | 6 sec tolerance | No discomfort after 30 second cycle |
| 3 | B | 1 sec tolerance | 3 sec tolerance | No discomfort after 30 second cycle |
| 4 | E | 1 sec tolerance | 10 sec tolerance | No discomfort after 30 second cycle |
| 5 | D | 2 sec tolerance | 25 sec tolerance | No discomfort after 30 second cycle |
| 6 | C2 | 2 sec tolerance | 8 sec tolerance | No discomfort after 30 second cycle |

FIG. 17

MODULATED WAVEFORM TREATMENT DEVICE AND METHOD

CROSS-REFERENCE TO RELATED APPLICATIONS

The application claims priority to U.S. Provisional Application No. 63/004,839, MICROCURRENT SKIN TREATMENT DEVICE AND METHOD, filed Apr. 3, 2020, which is incorporated by reference herein, in the entirety and for all purposes.

FIELD

The application relates to waveform modulation, and to modulated waveforms for microcurrent skin treatment and other energetic stimuli. More generally, the application relates to systems, devices, methods and functions for modulating electrical waveforms and energetic stimuli, and improvements in these technologies. Suitable uses include, but are not limited to, pulse modulated waveforms adapted for microcurrent skin treatment techniques, and other modulation of electrical and energetic stimuli. Uses of these improved technologies include cosmetic skin care and skin treatment applications, and other cosmetic and non-cosmetic applications adapted to address applicable regulatory requirements.

BACKGROUND

The skin is the largest organ of the human body, forming a physical barrier to the environment and providing important functions including insulation, temperature regulation and protection against micro-organisms, as well as touch, heat sensitivity, and other forms of sensation. The skin also regulates the passage of water and electrolytes, and produces vitamin D.

The outermost skin layer or epidermis covers the body's surface. Most of the epidermal cells are keratinocytes, which form an environmental barrier and synthesize vitamin D. The epidermis also includes melanocytes, which produce melanin to protect against harmful UV radiation, Merkel cells, which provide sensitivity to touch, and Langerhans cells, a type of white blood cell or macrophage that is part of the immune system, acting to protect the body against infection.

The epidermis surrounds the dermis. The structure of the dermis is provided by fibroblasts, which synthesize collagen and elastin proteins to form the extracellular matrix, with collagen fibers to provide strength and toughness, and elastin threads or filaments to provide elasticity and flexibility. The fibroblasts also produce proteoglycans, viscous proteins that provide hydration and lubrication, and regulate ionic binding and molecular transport. The dermis also includes macrophages and mast cells, part of the immune system, as well as the hair follicles, sweat and oil glands, nerve cells, and blood vessels.

The epidermis and dermis make up the cutis. Subcutaneous tissue connects the cutis to the underlying muscle and fascia, and to other connective tissue including the periosteum (covering the bones). The subcutis also includes elastin and adipose (fat) cells.

As the skin ages, loss of firmness and elasticity may be associated with a decrease in the production of Type I collagen (the most abundant form), as well as a reduction in elastin, proteoglycans, and other components of the extracellular matrix. Aging skin can also exhibit thinning, coloration, and reduced immune response.

A range of personal skin care products have been provided to help reduce certain aging effects, including topical products and hand-held devices for cleansing, exfoliating and smoothing the outer skin layers. A variety of galvanic (electric current-based) treatment devices are also known, for example as described in U.S. Pat. Nos. 5,147,297 A, 5,162,043 A, 5,298,017 A, 5,326,341 A, and 5,405,317 A, originally assigned to Alza Corporation of Palo Alto, California; U.S. Pat. No. 5,685,837 A, originally assigned to LTS-LohmanTherapie-Systeme of Neuweid, Germany; U.S. Pat. No. 6,584,349 B1, originally assigned to Viteris, Inc., of Fair Lawn, New Jersey; and U.S. Pat. Nos. 6,421,561 B1 and 6,653,014 B2, originally assigned to Birch Point Medical of Oakdale, Minnesota. Other stimuli are also possible, for example in the form of light energy as described in U.S. Pat. No. 9,079,022 B2, originally assigned to LED Intellectual Properties of Irvine, California.

In galvanic systems, one or more anode or cathode electrodes are arranged to produce an electric potential across the skin, providing current flow through the epidermal and dermal layers. Advanced microcurrent based devices can include a control circuit operably connected to the electrodes, in order to carefully regulate the current to promote ion transport and other biological effects; e.g., as described in U.S. Pat. Nos. 7,653,970 B1 and 10,046,160 B1 and U.S. Patent Publication No. 2007/0185431 A1, to NSE Products of Provo, Utah, each of which is incorporated by reference herein, in the entirety and for all purposes.

More generally, the skin's response to electric current flow involves a number of complex and interacting biological processes, and the full range of different treatment mechanisms have not all been recognized in the prior art. As a result, there is an ongoing need more progressive approaches to skin care, including microcurrent based skin treatment techniques developed with a better understanding of the underlying biological responses, and modulated electrical waveforms and energetic stimuli providing for improvements in treatment response and user comfort.

SUMMARY

A microcurrent skin treatment device is provided with one or more electrodes or emitters configured for electrical communication with the surface of a subject's skin. A voltage or current source is adapted to generate an electrical waveform for application to the skin surface, via the one or more electrodes or emitters. A controller can be configured for modulating consecutive pulses of the electrical waveform so that one or more of the pulse width, pulse period, pulse frequency and pulse amplitude varies with a random or pseudorandom component, or in another non-repeating or aperiodic manner.

In particular embodiments, for example, a set of different pulse parameters can be selected for modulating the waveform. The parameters can be randomly sequenced using a pseudorandom number generator, or other non-repeating, ordered set of variables, and applied to consecutive pulses in order to modulate the pulse width, pulse period, pulse frequency, or pulse amplitude of the waveform, or any combination thereof.

Alternatively, one or more selected pulse parameters can be modulated with a randomized or pseudorandom component, or otherwise varied in a non-repeating or aperiodic manner, independent of the sequence in which the pulses are applied. Methods for operating a microcurrent skin treatment device are also encompassed, along with randomizing functions and processes for modulating the applied waveform. Additional advantages and features of these techniques are set forth in the description that follows, and will be apparent to those skilled in the art upon examination of the specification, drawings and claims.

BRIEF DESCRIPTION OF THE DRAWINGS

FIG. 17 is a table summarizing data from a tolerability study for exemplary applications of a device for generating and applying modulated waveform stimuli, as described herein.

DETAILED DESCRIPTION

Figure 1:
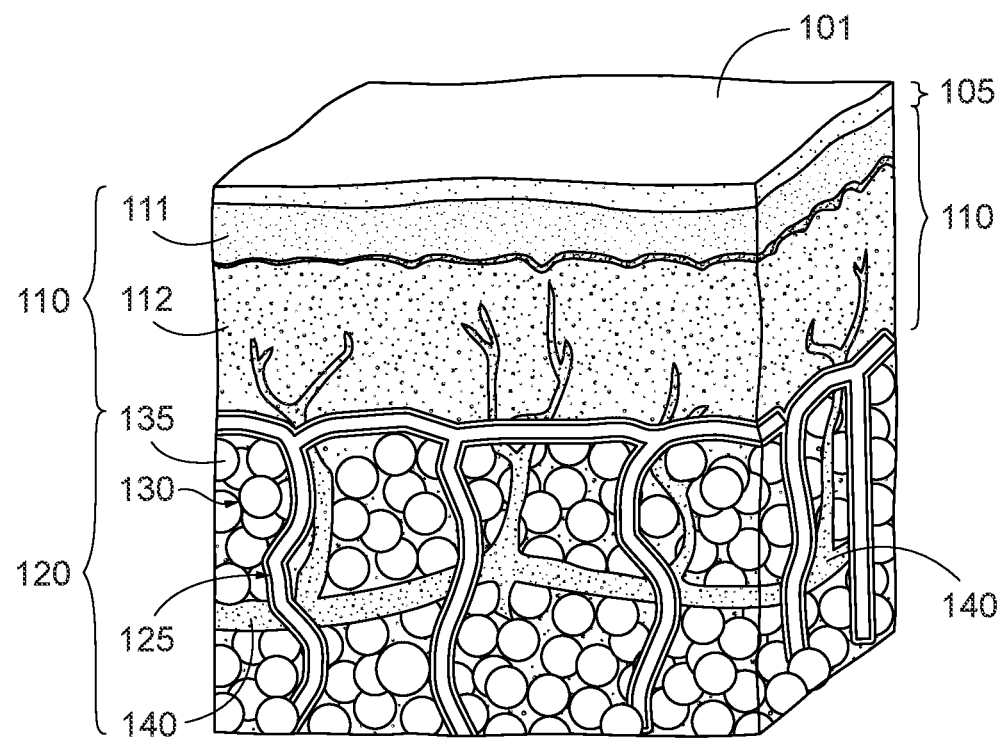
FIG. 1 is a sectional diagram illustrating representative components of human skin.

Although the present disclosure describes particular examples and preferred embodiments of the invention, persons skilled in the art will recognize that changes may be made in form and detail without departing from the scope of the claims. The various examples and embodiments are also described with reference to the drawings, where like reference numerals represent similar structural and functional components throughout the several views. These examples and embodiments do not limit practice of the invention as claimed; rather, the specification merely sets forth representative applications to different systems, methods and devices, and practice of the invention is not limited except as set forth in the appended claims.

Waveform Modulation for Energetic Skin Stimuli

Modulated waveforms can be used to define a range of energetic stimuli adapted for skin care and treatment, including galvanic and microcurrent-based treatments, and for other voltage or current-based devices. Waveform modulation can also be used to generate an LED, laser, or other electromagnetic stimulus, in radio frequency (RF), infrared (IR), near-ultraviolet (near-UV) or ultraviolet (UV) frequency range, or an ionizing radiation treatment, for cosmetic, non-cosmetic, medical or non-medical applications, consistent with all applicable legal and regulatory requirements. Acoustic stimuli can also be produced, for example in the subsonic, sonic, or ultrasonic ranges, or a combination of voltage, current, electromagnetic, and acoustic stimuli can be applied.

While various relationships between the modulated signal amplitude, treatment time and efficacy have been explored in certain prior art, there are still substantial design challenges in this area. In particular, there are no definitive modulation parameters that can be uniformly applied to improve the results of a particular skin treatment, across the full range of different potential applied stimuli. Nor have more generalized signal modulation techniques been identified to improve treatment efficacy, while reducing user discomfort and avoiding the possible tendency for homeostasis, which may substantially impact treatment benefits over time.

A randomized or pseudorandomized approach to waveform modulation is employed to address some or all of these issues. In this approach, a set of pulses in the waveform can be modulated or controlled to vary by pulse width, period, frequency, or amplitude, in a random, pseudorandom, or aperiodic manner. The modulation can include both pseudorandom variations based on computational algorithms, or "true" random variations based on probabilistic physical phenomena, such as atmospheric or thermal noise, background fluctuations, radioactive decay, or other quantum phenomena, and adapted to provide statistically random sequence of pulse variations, as described in the present specification, and as known in the art.

Randomized waveform modulation can be defined locally, over a given set of pulses within a treatment cycle or phase, or more globally, over a number of such phases making up a treatment cycle. Quantum-computer based randomization can also be used to generate the random pulse variation, or, more generally, a combination of random, pseudorandom, and quantum-based effects, selected to provide statistically randomized pulse parameters; for example, in either a non-repeating or aperiodic sequence, or without other recognizable patterns or regularity, i.e., any form of randomization that leads to a waveform that when analyzed over a relevant time period can be found to have some amount of statistical randomness as known in the field, in at least some aspect of the waveform. The random or pseudorandom sequence can be determined in real time, or predefined (e.g., using a random or pseudorandom generator to determine one or more such sequences), and then re-ordered for application to the subset of consecutive pulses defining each phase, or to the full set of consecutive pulses defining the a treatment cycle.

This randomized approach to waveform modulation can provide substantial improvements in skin health and appearance, while improving user comfort and potentially reducing the possible tendency for homeostasis; that is, the tendency to adjust to relatively stable equilibrium, in response to an applied stimulus. These improvements can be defined over a wide range of treatment criteria, using both quantitative user evaluations, a highly relevant measure for personal skin care and treatment technologies, and based on definitive clinical trial data, using on objective, blinded, clinical grader results, independent of the user evaluations, as described in detail below.

Device and Method Applications

FIG. 1 is a sectional diagram illustrating representative structural and functional components of human skin 100. As shown in FIG. 1, the skin (or "cutis") 100 includes an upper epidermal layer (or epidermis) 105 extending from the skin surface 101 to a lower dermal layer (dermis) 110. Together, the epidermis 105 and dermis 110 make up the cutaneous tissue or skin. The subcutaneous tissues comprise the subcutis (or hypodermis) 120, underlying the cutis 100.

Collagen fibers 125 extend from the lower dermis 110 through the subcutis 120, forming bands and sheets of connective tissue (fascia) connecting the skin (cutis) 100 to the underlying muscles and connective tissue. The dermis 110 also includes a papillary layer 111 and a reticular layer 112, formed of more loosely arranged and denser collagen fibers, respectively.

The subcutis 120 includes adipose tissues 130, for example in the form of lipocytes (fat cells) and intracellular or intercellular lipids, which can form lobules 135 and other structures between the collagen fibers 125. A network of small blood vessels or capillaries 140 provide circulation, extending from the subcutis 120 into the dermis 110.

Figure 2:
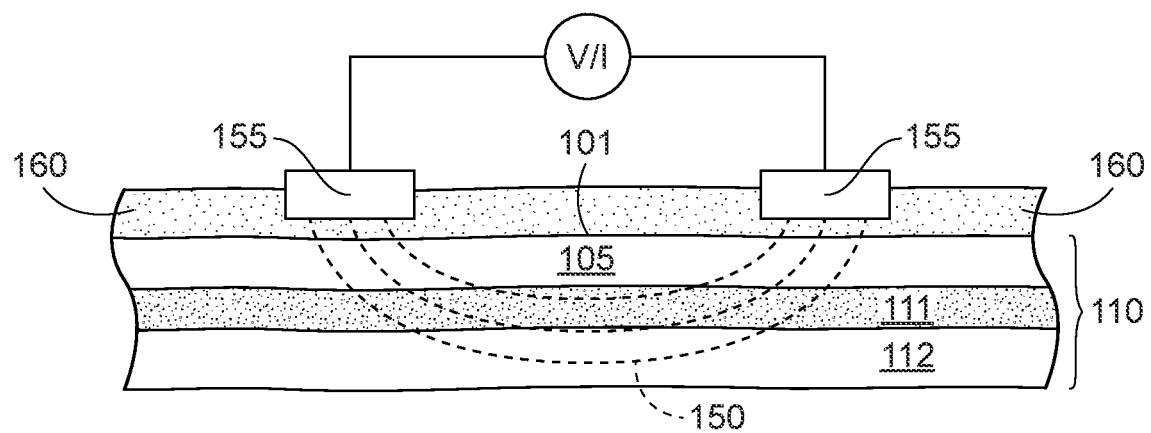
FIG. 2 is a sectional diagram illustrating current flow through representative skin layers.

FIG. 2 is a sectional diagram illustrating an electrical stimulus 150 propagating through different layers of the skin or cutis 100. For example, in one embodiment a current or microcurrent stimulus 150 can be generated by one or more electrodes or emitters 155 disposed along the skin surface 101. A gel or other topical skin treatment product 160 can be applied to the skin surface 101 to improve conductivity, and to provide the skin 100 with nutrients and other beneficial agents. It is also possible to use electromagnetic energy as a form of stimulus 150 to treat skin, for example in the form of radio frequency (RF), infrared (IR), optical or ultraviolet (UV) light (e.g., low-energy near UV light), or to provide an energetic stimulus 150 in the form of sonic, subsonic or ultrasonic acoustic energy. These energetic stimuli can be presented to the skin as a modulated waveform, similar to the modulated waveforms provided in the form of an electrical or current stimulus 150. Thus, electrical, electromagnetic and acoustic forms of energy are all within the teachings of the present disclosure, and any suitable combination of these energetic stimuli can be presented in the form of a modulated waveform.

As shown in FIG. 2, for example, an electrical stimulus 150 can be generated by applying a potential V (or current source I) between two or more electrodes or emitters 155, spaced along the outer surface 101 of the skin 100, either adjacent to or in direct contact with the skin surface 101. Alternatively, one or more electrodes 155 may be disposed on or adjacent the skin surface 101 in a particular location, for example on the face, arm, torso or leg, with another electrode 155 coupled remotely, for example via contact with the hand of the user (or other treatment subject), or elsewhere on the subject's body. In other applications, the electrical stimulus 150 can be applied with a single electrode 155; e.g., by applying an ungrounded (floating) potential waveform from one or more electrodes 155 to the skin surface 101, or by forming a current loop through the subject's feet or other ground contact.

Depending upon application, a potential V can be provided to the electrodes or emitters 155 to apply a current stimulus 150 to the top epidermal layer 105 of the skin 100, or a current propagating through the epidermal layer 105 to one or both of the (upper) papillary layer 111 and (lower) reticular layer 112 of the dermis 110. The electrical stimulus may also propagates into or through the subcutis 120, promoting a favorable response from both cutaneous and subcutaneous tissues. The stimulus 150 can thus promote a range of biological responses in epidermal, dermal (cutaneous) and subcutaneous tissues. Alternatively one or more (or all) of the electrodes or emitters 155 can take the form of LEDs or laser light sources (or other electromagnetic emitters) configured to provide a stimulus in the form of RF, IR, optical or UV light energy, or one or more acoustic transducers configured to provide a subsonic, sonic, ultrasonic, or other acoustic stimulus, or any suitable combination of electrical, acoustic, and electromagnetic emitters 155.

In particular examples, a DC (direct current) or pulsed DC potential V or current I is applied via the electrodes 155, so that the electrical stimulus 150 propagates in a particular direction through the skin 100. In other examples, an AC (alternating current) potential V of current I can be applied, so that the electrical stimulus 150 propagates back and forth, in alternating fashion.

The potential V can be applied as a steady-state (constant or alternating) voltage signal, or using a modulated waveform. Depending on application, the pulse width, amplitude, period and frequency of the applied voltage V or current I can all be controlled, either individually or in combination, in order to generate the electrical stimulus 150 as an AC, DC or pulsed DC current treatment for the skin 100 of the user or other subject. In particular applications, pulse with modulation (PWM) can be used to generate the stimulus 150 as a pulsed microcurrent signal, or other energetic stimulus 150, for example by applying a programmed, random or pseudorandom pulse width modulated (PRPWM) current or voltage waveform, or as a modulated electromagnetic or acoustic waveform, as described herein.

Figure 3:
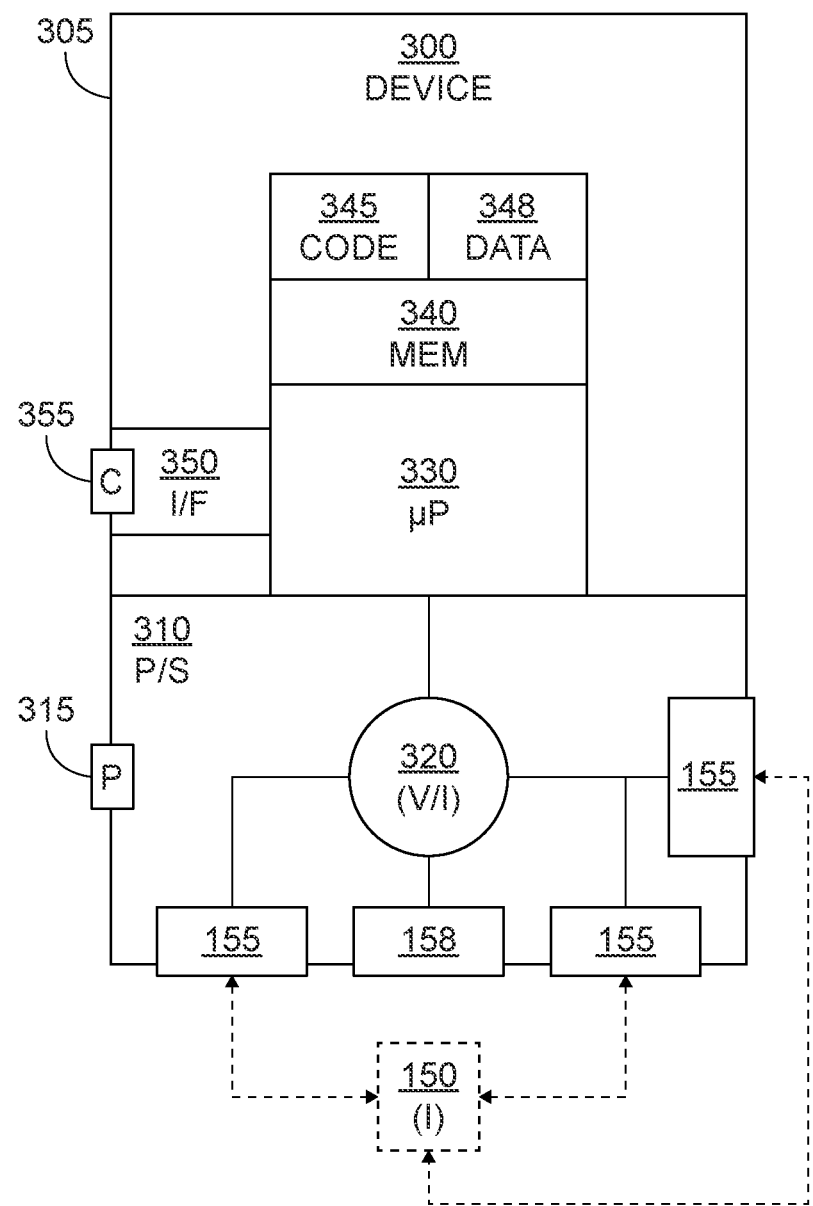
FIG. 3 is a block diagram of a microcurrent skin treatment device.

FIG. 3 is a block diagram of a representative device or apparatus 300 configured for microcurrent based skin treatment, or other energetic stimulus 150 according to FIG. 2. As shown in FIG. 3, microcurrent device 300 includes a housing 305 with a power supply (P/S) 310, a current or voltage generator (V/I) 320 electrically connected to one or more electrodes or other emitters 155, a microprocessor (P) based controller 330, memory 340 and an external communications interface 350.

Power supply 310 can be provided in the form of a rechargeable capacitor or battery system, for example with a power port 315 adapted for external wired or wireless (e.g., inductive) charging. The microprocessor controller 330 is provided in data communication with the memory 340, which provides storage for control code 345 and operational data 348. The communications interface (I/F) 350 can be adapted for both data and control communications with the controller 330, for example using a hard-wired communication port or wireless device 355.

In operation of device 300, power supply 310 provides power to the voltage or current generator (or source) 320, as well as the microprocessor controller 330, memory 340 and interface 350. Controller 330 is configured regulate the potential (V) or current (I) signal generated by source 320, for example by executing control code 345 stored in memory 340. Control parameters and other operational data 348 can be used for modulating the signal provided to each selected electrode or emitter 155, in order to deliver the desired amplitude, frequency, and pulse width modulation. One or more skin sensors 158 can also be provided, for example to measure skin surface temperature and resistivity, and to determine other skin conditions such as hydration, etc. Additional sensors 158 can also be provided to measure or monitor environmental conditions such as ambient temperature and humidity, etc.

The microprocessor controller 330 can also be adapted to monitor feedback signals from the electrodes or emitters 155, and for regulating the applied potential (V) or current (I) responsive to the feedback. Feedback-based regulation allows the controller 330 to maintain the desired electrical stimulus 150, taking into account the number and arrangement of electrodes 155 as well as the subject's skin type and related skin conditions such as resistivity, temperature, hydration, etc., for example as determined with additional data from one or more skin sensors and other environmental sensors 158. The controller 330 can also be adapted to regulate the current stimulus 150 transmitted through the subject's skin based the voltage (V) or current (I) signal actually applied to the electrodes 155, and on other operational and environmental conditions such as the presence or absence of a conductive gel or other skin treatment product between the electrodes 155 and the skin surface, and the record of other recent and historical treatment information recorded in the operational data 348.

Figure 4:
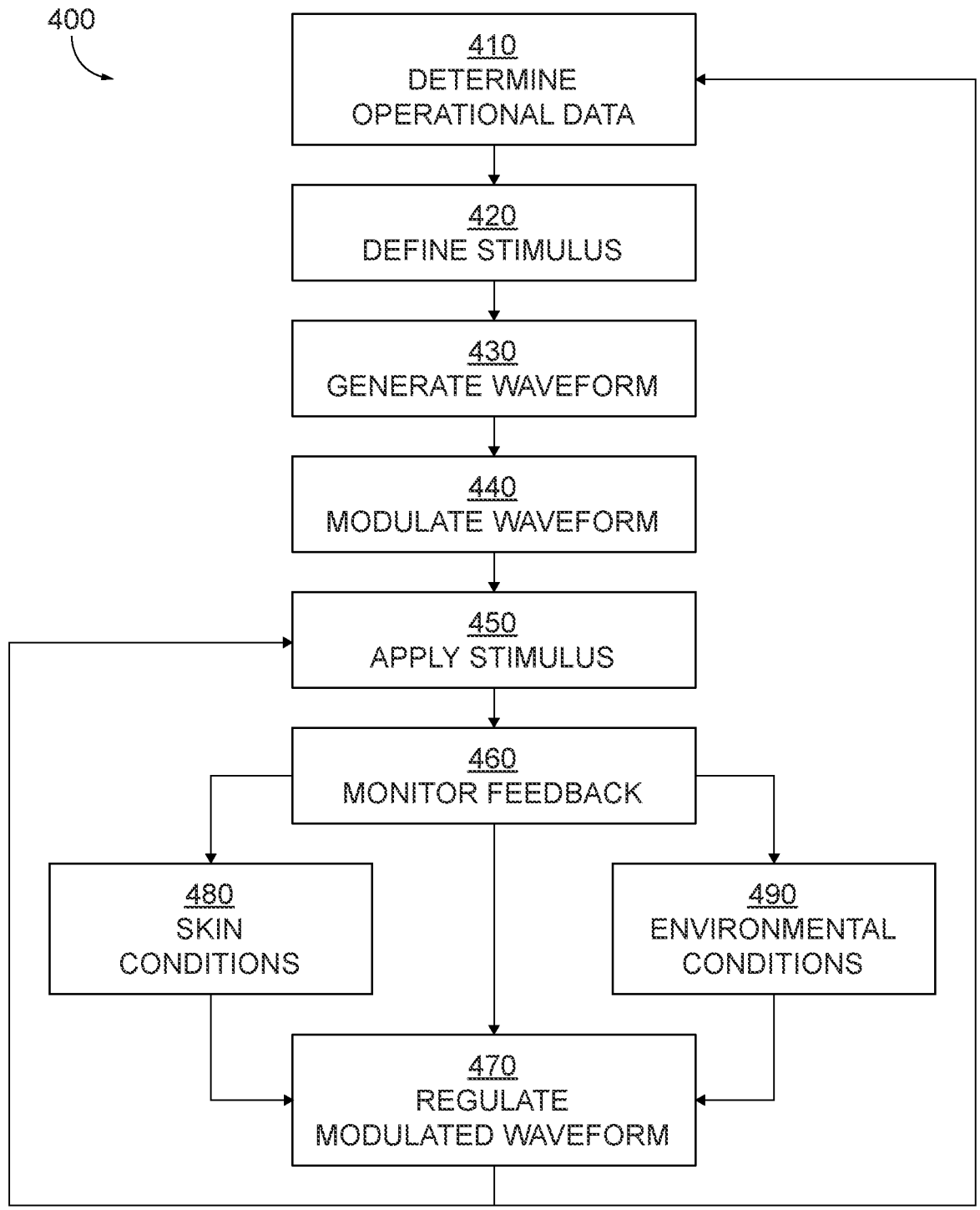
FIG. 4 is a block diagram of a method for microcurrent skin treatment.

FIG. 4 is a block diagram illustrating a representative method or process 400 for microcurrent-based skin treatment, for example using the device 300 of FIG. 3. As shown in the particular example of FIG. 4, method 400 comprises one or more steps of determining operational data (step 410), defining a stimulus (step 420), generating a waveform (step 430), modulating the waveform (step 440), and applying the stimulus (step 450), based on the modulated waveform.

Depending on application, method 400 may also include monitoring feedback (step 460), and regulating the modulated waveform (step 470); e.g. in order to reduce differences between the defined and applied stimuli. These steps can be performed in any order or combination, with or without additional procedures. For example, monitoring feedback (step 460) can also include monitoring sensor data, for example to determine skin conditions (step 480) and environmental conditions (step 490).

Determining operational data (step 410) can be performed as an initiation or start operation for method 400, for example by reading the operational data from memory. The operational data can include a set of operational parameters for performing the steps of method 400, or data used to generate such a parameter set. For example, the operational data may include stimulus data or parameters from which a desired stimulus can be selected or defined (step 420), and waveform data or parameters from which a desired voltage or current waveform can be generated (step 430).

The waveform data can also include a set of selected pulse parameters for modulating the waveform (step 440), so that the desired stimulus can be delivered or applied to the skin of a subject (step 450). The pulse parameters can be selected to characterize one or more pulse widths for "on" and "off" portions of the cycle, as well as pulse periods, frequencies and amplitudes.

The applied waveform may be either unipolar or bipolar; for example as defined based on the sign of the amplitude parameter, or by defining an absolute (non-negative) amplitude with a separate polarity parameter to determine the sign. The pulse modulation can be randomized by assigning selected parameters to consecutive pulses in a random or pseudorandom sequence, or by including a random or pseudorandom component in the modulated pulse parameters themselves, in order to generate a non-repeating or aperiodic sequence of modulated pulses.

For example, the pulse width, period, frequency, amplitude or other modulated pulse parameter may be aperiodic or non-repeating over a given set of pulses, so that the modulated parameter does not repeat at all, or does not repeat with any identifiable pattern or sequence, within the given subset or set. The aperiodic or non-repeating pulse parameter can be modulated over a set of consecutive pulses defining a treatment cycle with one or more treatment phases, or over a subset of consecutive pulses defining one or more of the phases.

The applied stimulus (step 450) can be monitored (step 460) by measuring the applied voltage or current flow through the electrodes or other emitters. Feedback parameters can be used to regulate the modulated waveform (step 470), for example by applying a hardware or software-based gain parameter to reduce any difference between the stimulus that is defined (at step 420), and the stimulus that is actually applied (at step 450). Feedback monitoring (step 460) can also include receiving sensor data used to determine skin and environmental conditions such as resistivity, surface temperature, hydration, ambient temperature, humidity, etc. (steps 480 and 490).

The operational data (step 410) can also include historical log data for prior operation of a suitable microcurrent device 300 according to method 400. For example, the log data can be recorded to characterize previously defined stimuli (step 420), and to record the parameters used for waveform generation (step 430) and modulation (step 440). Additional log data can provide records of stimuli that were actually delivered or applied in previous treatments (at step 450), as well as the electrode or emitter and sensor feedback (step 460), and additional parameters used to regulate the modulated waveform (step 470), to determine resistivity and other skin conditions (step 480), and to describe relevant environmental conditions (step 490).

Waveform modulation (step 440) can apply a variety of different pulse modification techniques. In the radio-frequency (RF) range, for example, amplitude modulation (AM) and frequency modulation (FM) are commonly used. In these techniques, the modulated waveform is typically a sinusoidal carrier wave generated at a particular carrier frequency, for example in the kilohertz (kHz), megahertz (MHz), or gigahertz (GHz) range.

In amplitude modulation (AM), the amplitude of the carrier wave can be varied according to an analog (e.g., audio-frequency) signal. The modulated carrier signal is demodulated at the receiver, separating the information-carrying modulation frequencies from the carrier wave. For analog modulations in the audio-frequency range of about 1-10 kHz, typical carrier frequencies extend from the tens of kilohertz (kHz) into the tens of megahertz (MHz) and above.

In frequency modulated (FM) techniques, the instantaneous frequency of the carrier wave is varied, rather than the amplitude. For audio-range applications, FM carrier frequencies traditionally extend from about ten megahertz (10 MHz) and above into the gigahertz (GHz) range. Frequency shift keying (FSK) can also be applied across a range of both lower and higher frequencies, for example to encode digital signals by shifting the carrier frequency among a selected set of discrete adjacent frequencies.

In skin treatment applications, the stimulus is not limited to a narrow-band carrier wave, by can also be defined (step 420) in terms of a pulsed waveform (step 430), to which programmed, randomized pulsed waveform modulation (PRPWM) can be applied (at step 440) in order to deliver the desired stimulus (step 450) to the subject's skin. Programmed, randomized pulsed waveform modulation can also be adapted to ensure charge and power balancing, and to incorporate a more advanced understanding of the body's underlying biological mechanisms, including the effects of randomized pulse width modulation on the body's homeostatic response.

Pulsed Waveform Modulation

Figure 5:
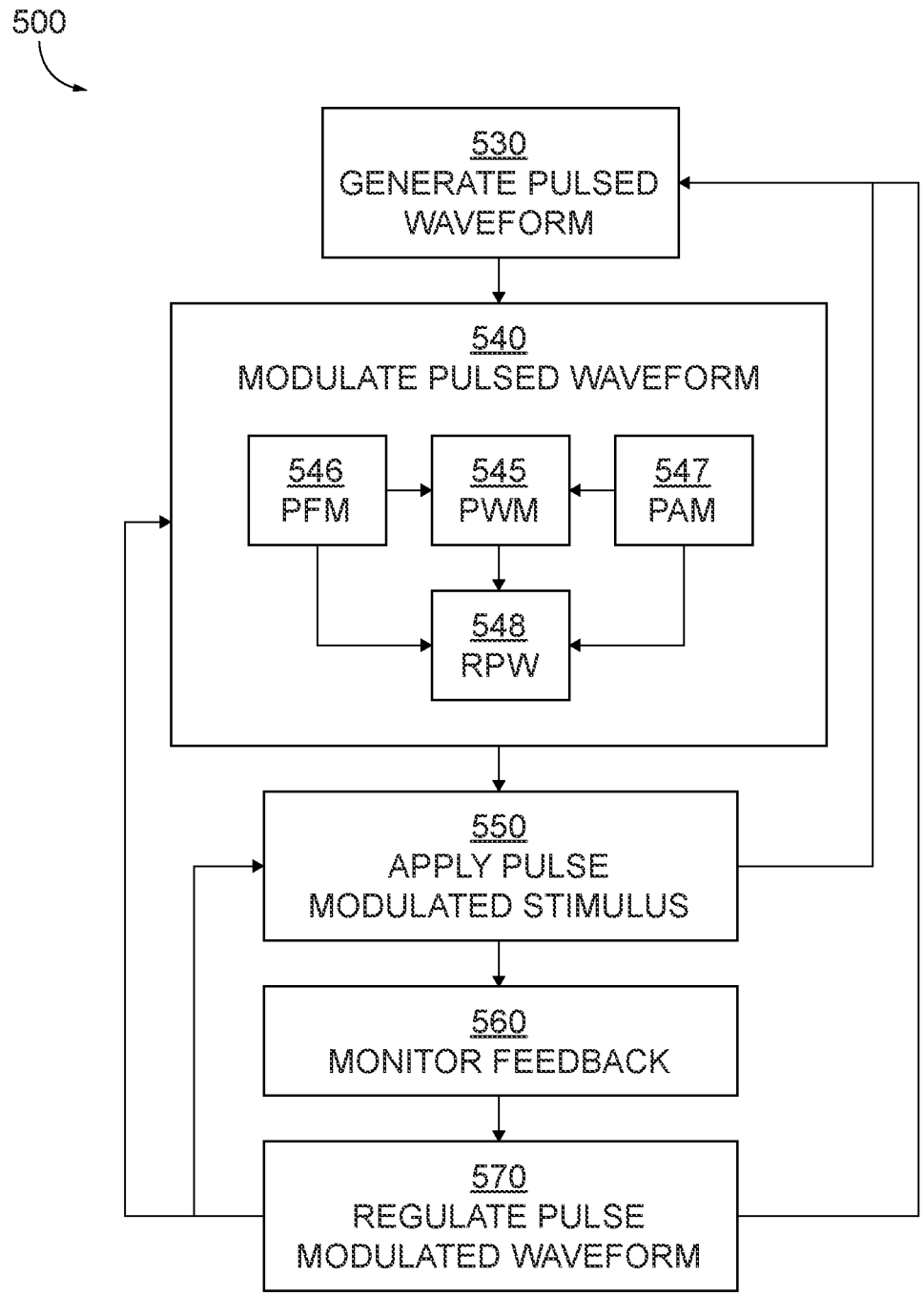
FIG. 5 is a block diagram for a method for pulsed waveform modulation.

FIG. 5 is a block diagram of a method or process 500 for pulsed waveform modulation. For example, method 500 may be used to operate a device 300 having one or more electrodes or emitters 155, as shown in FIG. 3, and adapted to apply a pulse modulated electrical stimulus 150 to a subject's skin, as shown in FIG. 2. Similarly, method 500 can also be adapted to modulate a waveform for microcurrent-based skin treatment, for example according to method 400 as shown in FIG. 4.

As shown in FIG. 5, method 500 includes generating a pulsed waveform (step 530), modulating the waveform (step 540), and applying a pulse modulated stimulus (step 550). These steps can be performed in any order or combination, with or without additional processes. For example, method 500 may also include monitoring a combination of sensor and electrical feedback (step 560), and regulating the modulated waveform (step 570) based on the feedback; e.g., in order to match the predefined and applied stimuli according to steps 420 and 430-470 of method 400.

Generating a pulsed waveform (step 530) comprises providing a pulsed electrical signal, for example using a voltage or current generator 320 as shown in FIG. 3. The pulsed waveform can be sinusoidal or non-sinusoidal, for example a square wave, rectangular wave, saw-tooth, or triangular waveform, or other periodic or aperiodic function. The waveform can also be generated with either positive or negative polarity, or in bipolar form, and may be referenced to ground or superposed on a DC signal with either positive or negative bias.

Pulsed waveform modulation (step 540) encompasses a range of modulation techniques including pulse width modulation (PWM; step 545), pulse frequency modulation (PFM; step 546), pulse amplitude modulation (PAM; step 547), and combinations thereof. In particular examples, random or pseudorandom pulse width modulation (RPW) 548 can be applied to enhance biological response when the stimulus is applied to a subject's skin, (step 550), and to reduce the tendency for homeostasis.

Pulse width modulation (PWM; step 545) is a technique for selectively distributing power over the individual pulses in a pulsed waveform or carrier wave, according to a desired (e.g., analog or digital) modulation function. The average value of the power delivered is determined according to the time integral of the modulated voltage and current waveforms, while the instantaneous power is determined by the respective amplitudes at a particular time. Since the pulse width is also reflected in the length or duration of the signal, pulse width modulation can also be described as pulse duration modulation (PDM).

In pulse frequency modulation (PFM) 546, the frequency of the pulsed waveform can be varied either independently of the pulse width and amplitude, or in combination. Variations in the frequency are reflected by changes the period between consecutive pulses, and can be performed according to either an analog or digital modulation signal, for example by frequency-shift keying (FSK), in which the pulse-to-pulse frequency is varied among a selected set of discrete digital frequency changes.

In pulse amplitude modulation (PAM) 547, the amplitude of the pulsed waveform (or carrier wave) can be varied from pulse to pulse, either independently of or in combination with one or more the pulse width, pulse period and carrier frequency. Pulse amplitude modulation (PAM) can also be applied as an analog or digital modulation technique, for example by amplitude-shift keying (ASK), in which the pulses are modulated according to a selected set of discrete amplitudes, each assigned to a different digital value.

In randomized pulse width modulation (RPW; step 548), the widths of individual waveform pulses are modulated according to a randomized or pseudo-random scheme. The pulse width and duty cycle of the waveform can be randomized independently of the pulse frequency and amplitude, or the techniques can be combined, as described below.

The modulated waveform can be applied (step 550) in the form of an electrical voltage or current, for example as delivered to a subject's skin by one or more electrodes or emitters 155, as shown in FIG. 3. Feedback from the electrodes 155 and one or more sensors 158 can also be monitored (step 560), in order to determine differences between the defined stimulus and the stimulus that is actually applied.

The modulated pulse width can be regulated (step 570) according the feedback, in order to match the applied stimulus to the desired effect. For example, the amplitude of a given voltage stimulus can be regulated according to the skin's resistivity, in order to deliver a desired current stimulus. Alternatively, any combination of the pulse width, frequency and amplitude of the applied stimulus can be regulated according temperature, hydration level, and other skin and environmental conditions, or based on the presence or absence of a topical treatment between the treatment electrodes (or other emitters) and the skin surface.

Randomized Pulse Modulation

Randomized pulse width modulation (RPW) 548 can also encompass any combination of pulse width modulation (PWM) 545, pulse frequency modulation (PFM) 546, and pulse amplitude modulation (PAM) 547, as described above. For example, a set of individual "on" and "off" pulse widths can be defined within a particular range, and then randomly sequenced for application to consecutive pulses in the waveform, using a machine-based pseudorandom number generator (PRNG), or a hardware-based ("true") random number generator (HRNG).

Alternatively, the pulse widths can be defined with a randomized or pseudorandom component, and applied sequentially to the consecutive pulses, with or without an additional sequential randomization step. Similar randomization techniques can also be used to modulate of the pulse amplitude, pulse period and frequency, producing a modulated waveform with any suitable combination of constant, deterministic and random or pseudorandom pulse amplitude, frequency and width.

If the total pulse period ("on" plus "off") period is fixed, for example, the pulse width can nominally be modulated independently of the instantaneous (pulse-to-pulse) carrier frequency, although the changing pulse width will still be reflected in the Fourier transform. If the total period ("on" plus "off") is not fixed, both the pulse width and the instantaneous carrier frequency will change from pulse to pulse. Similarly, while the pulse amplitude can nominally be modulated independently of the pulse width and instantaneous carrier frequency (based on the pulse-to-pulse period), the frequency of any amplitude modulation will be reflected as sidebands in the Fourier transform. All of these randomized modulations of the applied stimulus can enhance the skin's response, and provide additional benefits for skin treatment, as described according to the various examples herein.

Randomized Pulse Modulation

Figure 6:
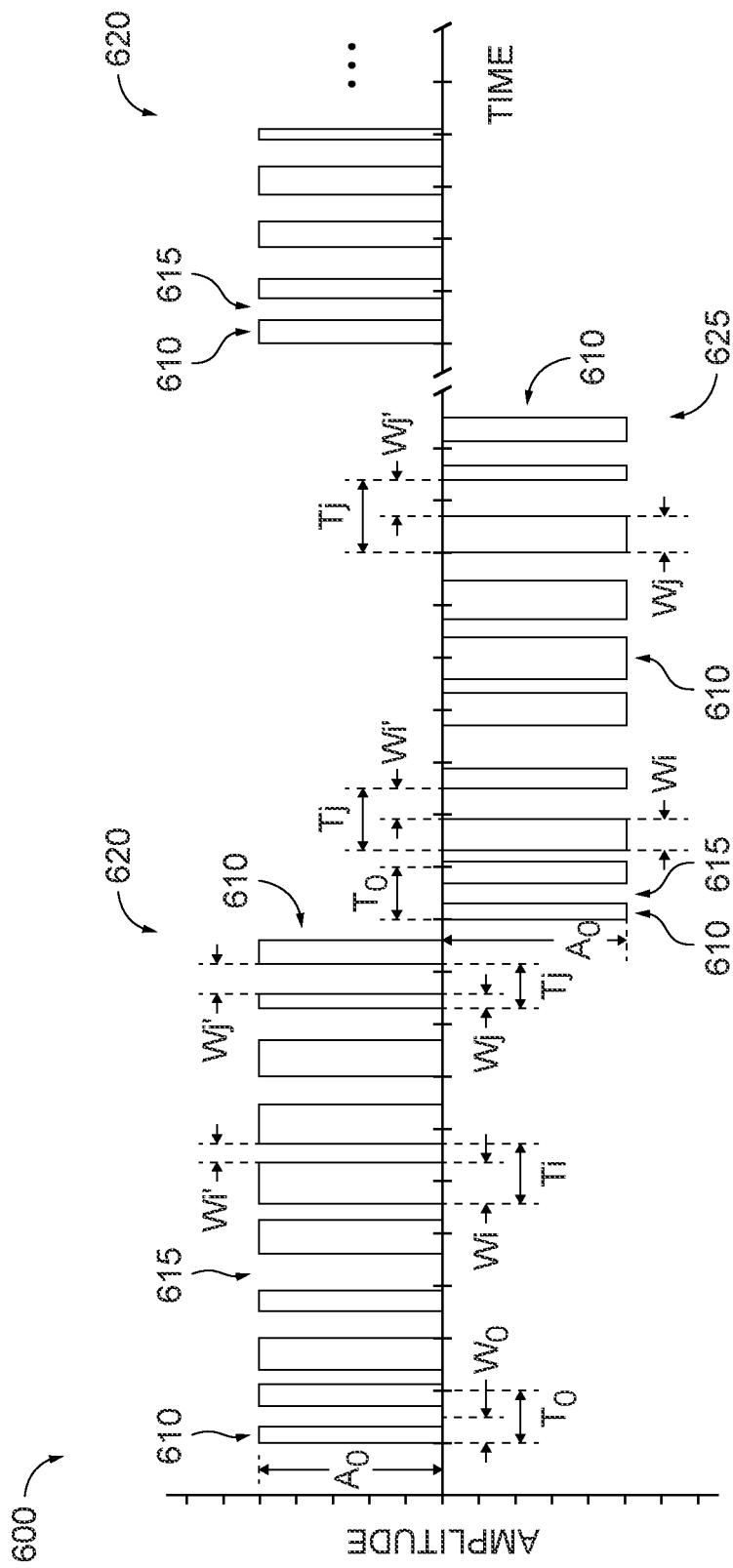
FIG. 6 is an amplitude-time plot of a waveform with randomized pulse width modulation.

FIG. 6 is an amplitude-time plot of a pulse width modulated (PWM) waveform 600, with randomized pulse width modulation (RPW) modulation. The vertical axis represents the pulse amplitude, in arbitrary units. The horizontal axis represents time, also in arbitrary units.

In the particular example of FIG. 6, programmed randomized pulse width modulation (PRPWM) is used. Waveform 600 is generated as a series of individual pulses 610 with modulated "on" pulse width W=Wi, Wj, etc., and corresponding "off" pulse segments 615 with width W'=Wi', Wj', etc. The nominal pulse amplitude is substantially constant at A=A0. The instantaneous carrier frequency f=1/T varies from pulse to pulse according to the total (on+off) period T; that is, with Ti=Wi+Wi', Tj=Wj+Wj', etc.

The pulses 610 in waveform 600 can be generated in unipolar or bipolar form. For example, waveform 600 may define a treatment cycle that includes one or more alternating trains or phases 620 and 625 of consecutive positive or negative polarity pulses 610, with individual pulses 610 separated by "off" segments 615 as shown in FIG. 6. In this particular example, pulses 610 have positive amplitude +A0>0 in the first (positive) phase 620, and negative amplitude −A0<0 in the second (negative) phase 625.

In unipolar applications, waveform 600 can define a treatment cycle that includes a number of positive pulses 610 (amplitude +A0>0) arranged in one or more positive phases 620, or a number of negative pulses 610 (amplitude −A0<0) arranged in one or more negative phases 625. The pulse number and amplitude may vary from phase to phase, and polarity of the phases 620 and 625 can be reversed, without loss of generality. Pulses 610 can also be generated in bipolar form; e.g., with a positive pulse segment transitioning to a negative pulse segment, or vice-versa, and a bias can be applied to the baseline amplitude, with pulse amplitudes ±A0 measured from the bias value.

In the particular example of FIG. 6, both the "on" pulse widths W=Wi, Wj and the "off" segment widths Wi', Wj' vary with respect to the nominal width W0, according to a random or pseudorandom modulation function. The first phase 620 may have the same number (N) of pulses 610 as the second phase 625, or a different number, and the sequences of pulse widths Wi, Wi', Wj, Wj' may be the same or different. For example, the same set of randomized pulse widths Wi, Wi', Wj, Wj' can be used for both phases 620, 625, in the same order, so that the pulse trains are the same except for polarity, with periods Ti, Tj and on/off pulse widths Wi, Wi'; Wj, Wj' being the same for each sequences of pulses 610 in both positive phase 620 and negative phase 625, in the same order. Alternatively, the sequence of pulses widths can be randomized, or the sequence can be shifted or reversed, or otherwise change from phase to phase, so that Ti, Tj and on/off pulse widths Wi, Wi'; Wj, Wj' vary from pulse to pulse 610 in each phase 620, 625, in any order.

The power delivered by waveform 600 depends upon the pulse frequency (f=1/T0), the pulse height or amplitude (A), and the duty cycle, which is determined by the widths of the on and off segments of each individual pulse 610 (Wi, Wi', Wj, Wj', etc.). In current-based applications, the power can be expressed a product of the current and voltage P=I×V, where the pulse amplitude typically represents either the voltage (V) or the current (I), or the power itself (P). More generally, skin tissue may have a complex impedance reflecting a combination of resistive and reactive (capacitive and inductive) effects, and the power function will account for both the frequency and phase of the current and voltage signals.

The duty cycle of the modulated waveform 600 is determined by the "on" pulse width Wi, Wj, as compared to the respective period Ti, Tj, over the total treatment time in each phase 620, 625. In square wave pulses, for example, the widths of the on and off pulse segments are equal, and the duty cycle is 50%. For randomized pulse with modulation, as described here, the duty cycle can vary from pulse to pulse and from phase to phase, or the duty cycle can be constrained be to have a particular value based on the integrated pulse width for each phase, for example around 50%, or anywhere from a few percent or less (≤1-10%), up to ninety percent or more (≥90%). Similar techniques can also be applied to modulate the pulse period (T) and amplitude (A) in order to main maintain charge balance.

In particular applications, each phase 620, 625 may include from one to ten or more individual pulses 610 (N), delivering a current (I) of up to 100-250 microampere (μA), or more. The individual "on" and "off" pulse widths (Wi, Wi', Wj, Wj') can vary from a few milliseconds or less (T≤1-10 ms), up to a few tenths of a second or more (T≥0.1-1.0 s).

Since the pulse widths are randomized, the power function also varies from pulse to pulse, and the variations may be aperiodic (or non-repeating) both within a particular phase, and over consecutive phases 620, 625. For example, the pulse widths can be modulated within a selected range of the nominal width W0; e.g., from about 0.20×W0 or 0.50×W0 to about 2.0×W0, or from about 0.1×W0 to about 10×W0, or from about 0.01×W0 (or less) to about 100×W0 (or more).

More generally, the pulse width, period, frequency, or amplitude (or other modulated pulse parameter) may vary over a similar range, as compared to the average or nominal value of the modulated parameter. The average of nominal values can be defined or determined across a subset of consecutive pulses defining a phase of a selected treatment cycle, or across the set of consecutive pulses defining the treatment cycle itself. The variation in the modulated pulse parameter can be 1% or less of the nominal or average value, or at least 1% of the average or nominal value. The variation in the modulated pulse parameter can be at least 10% or at least 20% of the nominal or average value, for example up to 50% of the nominal or average value, up to 100% of the nominal or average value, or up to two times the nominal or average value. The variation in the modulated pulse parameter can also extend up to ten times the nominal or average value, or up to one hundred times the nominal or average value, or more.

The variation can be aperiodic non-repeating fashion over a given set or subset of pulses, so that the modulated parameter does not repeat at all, or does not repeat with any identifiable pattern or sequence, within the given subset or set. Sets or subsets of consecutive pulses 610, can be defined over a treatment cycle comprising one or more treatment phases 620, 625, or over one or more phases 620, 625 within a treatment cycle. For example, the pulse widths (or other pulse parameters) can be assigned to consecutive pulses 610 in each of the phases 620 or 625 using a random, pseudorandom, or predefined sequence, such that the pulse parameters are aperiodic or non-repeating within each individual phase 620, 625, or across one or more phases 620, 635 that make up a treatment cycle.

Alternatively, the pulse parameters can be non-repeating or aperiodic as defined globally, over the complete set of pulses 610 defining a treatment cycle including any number of individual phases 620, 625. For example, a suitable random or pseudorandom sequence can be defined in real time, and assigned to consecutive pulses 610 in one or more phases 620, 625, or a suitable sequence can be predefined using a random or pseudorandom pattern, and then rearranged or reordered for each phase 620, 625. Individual pulses 610 can also be assigned random or pseudorandom components, or using a predefined random or pseudorandom sequence or pattern, so that the modulated parameters are non-repeating or aperiodic over the individual pulses in each phase 620, 625, or over a treatment cycle including any number of such phases.

The treatment time varies depending on the pulse frequency (f) and period (T), as well as the number of individual pulses 610 in each phase 620, 625. In some applications, for example, ten or more (N≥10) pulses 610 can be sequentially distributed over each phase 620, 625 with an average pulse period of about 120 ms, and delivered over a time period of about 1.2 s (1200 ms). Alternatively, the number of pulses per phase may vary from one to about 100 or more. The average pulse period may vary from about 50 ms or less to about 500 ms or more, corresponding to treatment times ranging from a second or less up to ten seconds or more.

The total treatment cycle time depends on the average pulse period, the number of pulses per phase, and the number of phases that are applied. A typical treatment cycle may include up to ten phases or more of each desired polarity, with a total treatment cycle time ranging from up to ten seconds or more (e.g., ≥10 s). In other applications the number of phases varies, for example from one to ten or more, or from ten to fifty or more, or from fifty to one hundred or more, and the total treatment cycle time can range from about a few seconds or less (≤1-10 s) to a few minutes or more (≥1-10 min).

Charge Balance

The randomized modulating function can be constrained or controlled so that the absolute value of the integrated pulse height is the same in each successive phase 620 or 625, in order to achieve charge balance. When delivering electrical stimuli such as microcurrent skin treatments, for example, the integrated current or charge applied in each positive-polarity phase 620 can be constrained to equal the absolute value of the integrated current or charge delivered in each negative polarity phase 625, so that the net current and charge delivered to the skin are balanced.

In charge balanced applications, the integrated power delivered in successive phases 620, 625 is substantially the same, and the net integrated charge and current are at, near, or approaching zero (that is, within a selected limit or minimum threshold value of zero). Alternatively, the modulation function may be unconstrained with respect to one or more parameters (e.g., pulse width, period, frequency, or amplitude), and the integrated charge or current may vary not only from pulse to pulse, but also from phase to phase.

Other Modulated Waveforms

Figure 7A:
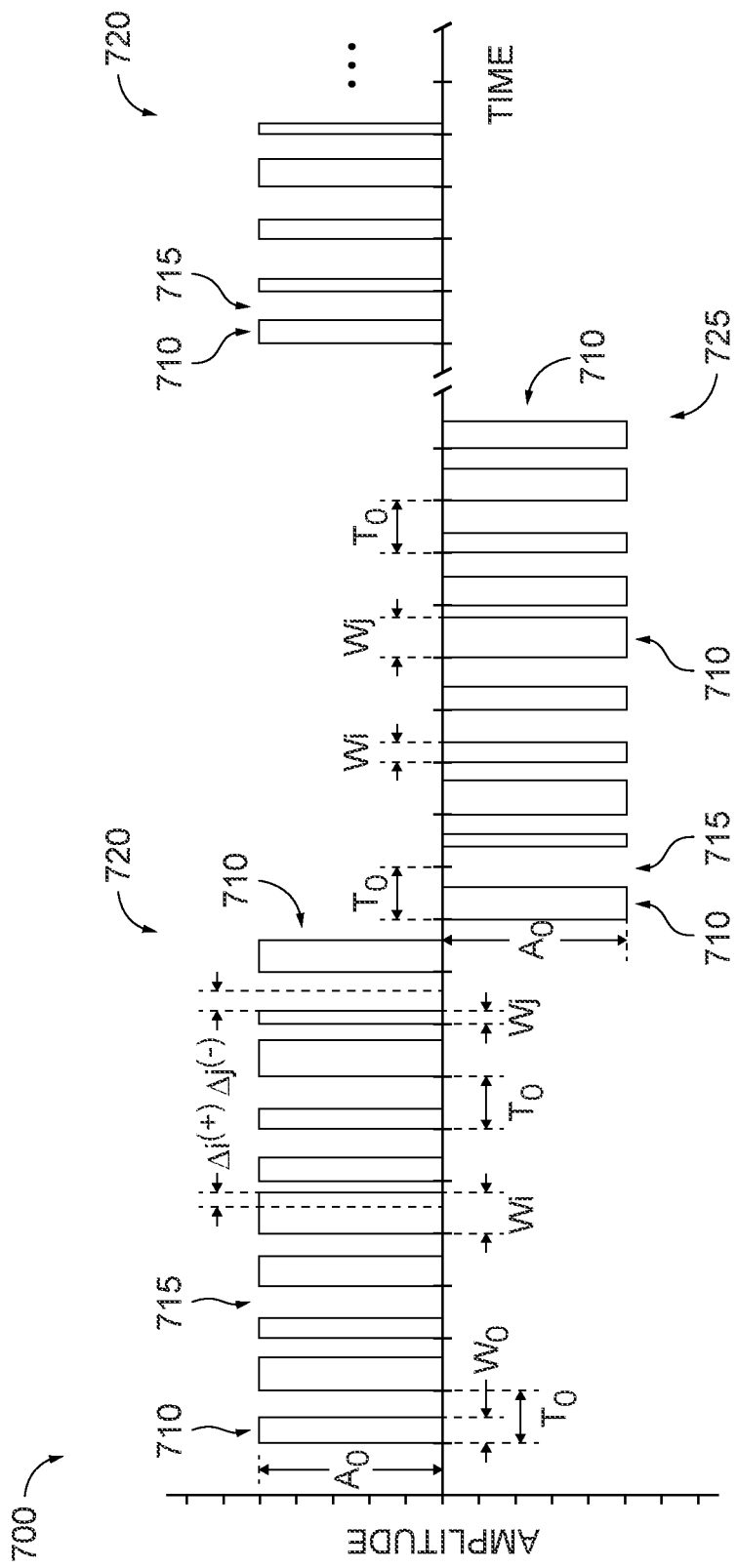
FIG. 7A is an amplitude time plot of a randomized pulse width modulated waveform with fixed carrier frequency.

FIG. 7A is an amplitude time plot of a randomized pulse width modulated (RPW) waveform 700, with substantially constant pulse period T0 and carrier frequency f=1/T0. The vertical axis represents the pulse amplitude and horizontal axis represents time, with both axes scaled in arbitrary units.

As shown in FIG. 7A, waveform 700 is generated as a series of individual pulses 710 with fixed or nominal amplitude A=A0, distributed over a number of phases 720, 725 having opposite polarity. The individual pulses 710 have variable ("on") pulse width W=Wi, Wj, etc., separated by variable-width "off" pulse segments 715, for which the amplitude is either substantially zero, or fixed at a selected bias value. In this particular example, some pulses 710 have a larger than nominal width Wi>W0, corresponding to a positive pulse width deviation $\Delta i^{(+)}=+|Wi-W0|$, and others pulses have a relatively smaller width Wj<W0, corresponding to a negative deviation $\Delta j^{(-)}=-|W0-Wj|$.

The individual deviations in period Ai, Aj may also vary among the different phases 720, 725, as shown in FIG. 7A. Each of the pulse widths Wi, Wj can thus be different, so that the modulated waveform 700 is non-repeating and aperiodic over each treatment phase 720, 725, or over an entire treatment cycle including any number of phases 720, 725. Alternatively, the values of the individual pulse widths W=Wi, Wj, can be randomly sequenced within each phase 720, 750, or across the treatment cycle, or in another suitable non-repeating or aperiodic fashion.

The modulation function in FIG. 7A is constrained so that adjacent pulses 710 remain distinct in time; for example, with positive deviation limited by $|\Delta i|<|T-W0|$, and negative deviation limited by $|\Delta j|<|W0|$. The modulation function can also be constrained to maintain a selected average duty cycle over each treatment phase 720, 725, and for charge, current and power balance, as described above. More generally, any waveform 700 or other waveform described here can be modulated to provide any number of positive, negative or bipolar pulses over any number of consecutive phases, in which each individual pulse may have a nominal, increased or decreased pulse width W=W0, Wi, Wj, etc.

Figure 7B:
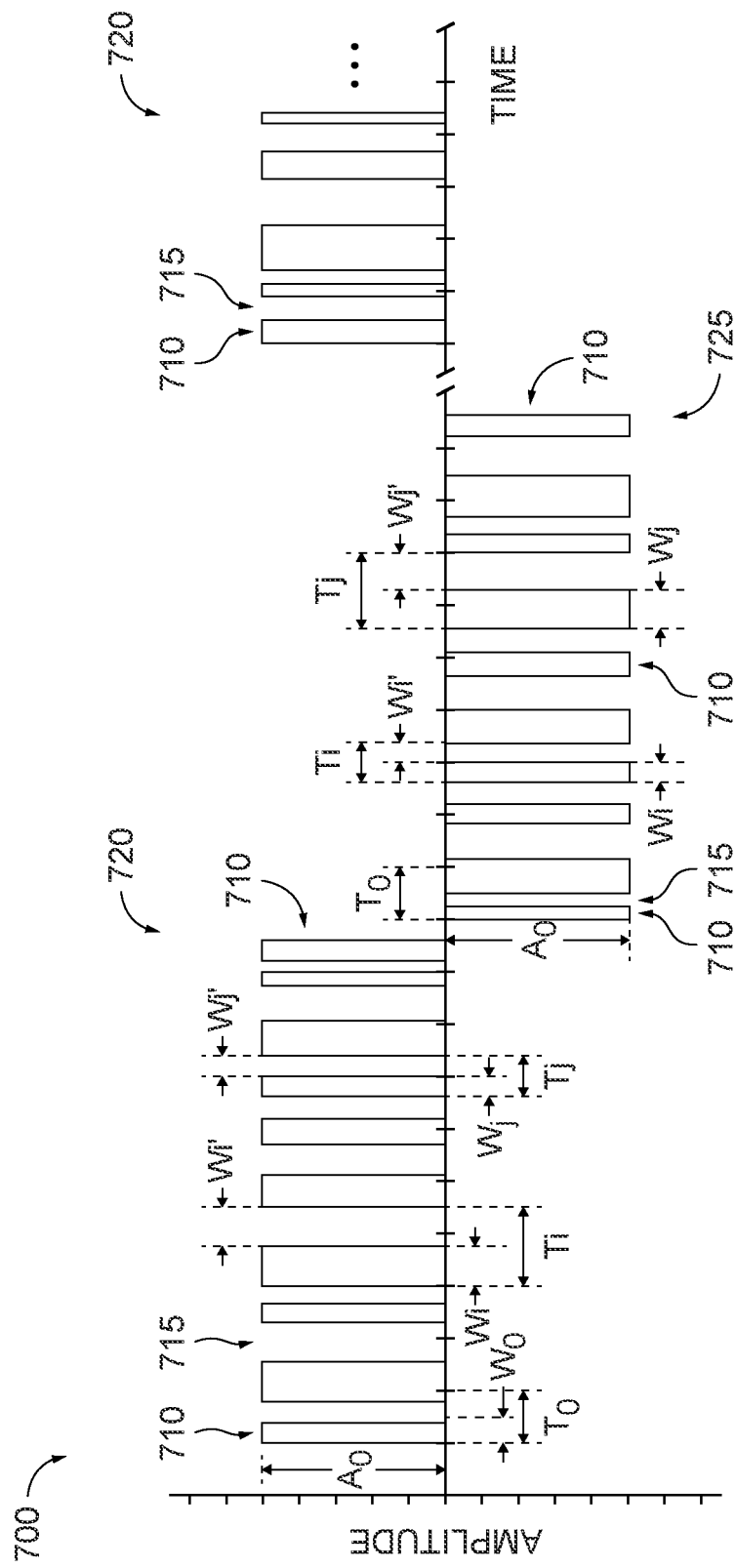
FIG. 7B is an amplitude-time plot of a pulse width modulated waveform with matched on-off pulse width.

FIG. 7B is an amplitude-time plot of a waveform 750 with matched on-off pulse width modulation. In this example, the pulse amplitude is fixed at an arbitrary nominal value A=A0, as shown on the vertical axis, with variable pulse widths Wi, Wj along on the horizontal, also in arbitrary units.

The pulses 710 making up waveform 750 are distributed among a number of consecutive phases 720, 725, with either positive or negative polarity as shown. The "on" pulse width W=Wi, Wj of each individual pulse 710 matches that of the corresponding "off" pulse segment 715, and the pulse period T ("on"+"off") varies accordingly (e.g., Ti=2×Wi, Tj=2×Wj, etc.).

In this particular example the duty cycle of each individual pulse 710 is fixed at 50%, since the widths of the on and off pulse segments are matched, while the instantaneous frequency f varies with the total pulse period (f=1/Ti, f=1/Tj, etc.). The modulation function is constrained to achieve charge, current and power balance, and so that the total integrated pulse width and treatment time is the same in each consecutive phase 720, 725. More generally, any waveform 750, or other waveform described here, can be modulated to have matched or unmatched on and off pulse widths, with fixed or variable pulse amplitude, pulse period, and carrier frequency.

Figure 8A:
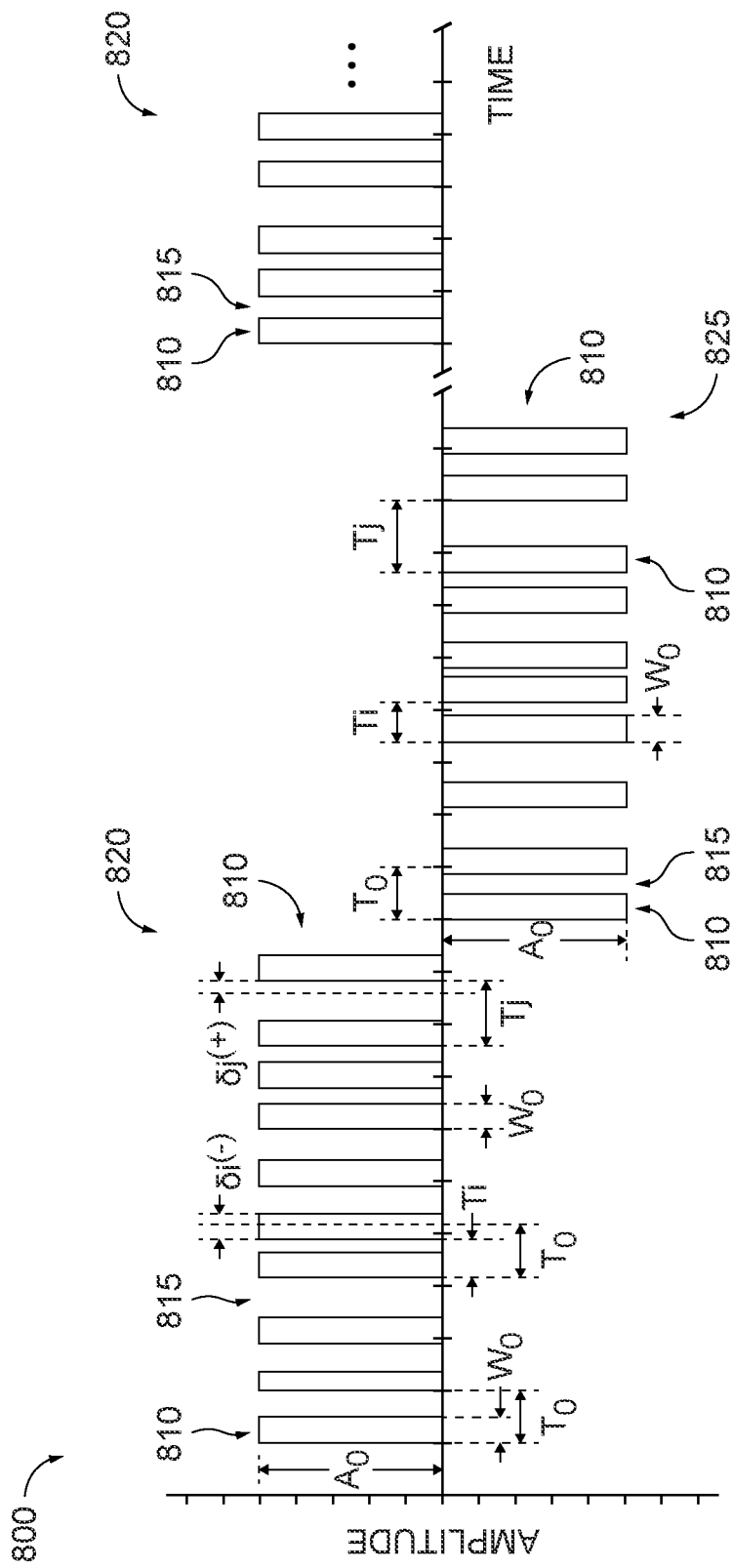
FIG. 8A is an amplitude-time plot of a waveform with randomized pulse frequency modulation.

FIG. 8A is an amplitude-time plot of a pulse-frequency modulated (PFM) waveform 800, with randomized pulse period and frequency (RPF). In this example, the nominal amplitude of each pulse 810 is substantially constant (A=A0; vertical axis), with fixed "on" pulse width W0 (horizontal axis, in arbitrary units). The carrier frequency is modulated by varying the length of the "off" pulse segment 815, as reflected in the pulse period T=Ti, Tj, etc., and the instantaneous (pulse-by-pulse) frequency varies accordingly (e.g.; f=1/Ti, F=1/Tj, etc.).

As shown in FIG. 8A, a series of frequency modulated pulses 810 can be arranged into consecutive phases 820 and 825, with either the same or alternating (e.g., positive and negative) polarity. Some pulses 810 have a less than nominal period Ti<T0, corresponding to a negative pulse period deviation $\delta i^{(-)}=-|T0-Ti|$, and a relatively higher instantaneous (pulse-to-pulse) frequency f>1/T0. Other pulses 810 have a greater than nominal period Tj>T0, corresponding a positive deviation $\Delta j^{(+)}=+|Tj-T0|$, and a relatively lower instantaneous frequency f<1/T0.

In the particular example of FIG. 8A, the nominal "on" pulse width W0 and amplitude A0 are substantially the same for each pulse 810 in waveform 800. Thus, the modulation function need not be further constrained for charge, current and power balancing between successive phases 820 and 825, as long as the number of pulses (N) is the same. The modulation function can also be constrained to preserve the phase application time N×T0, so that successive phases 820, 825 are equally spaced in time. In other applications, the pulse width and amplitude of any waveform 800 or other waveform described here can also be modulated to provide different phase application times, either independently from the pulse period and carrier frequency, or in combination.

Figure 8B:
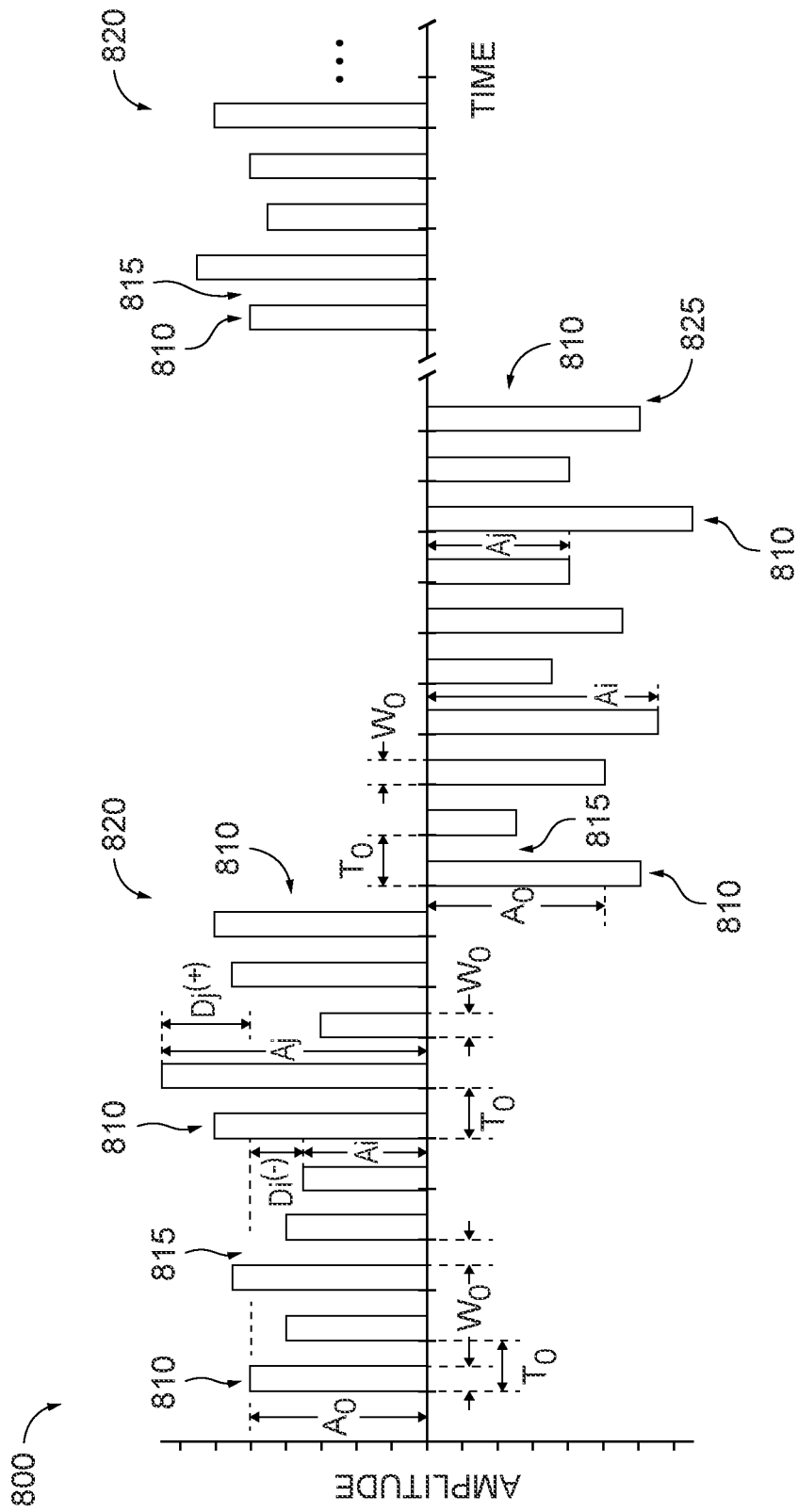
FIG. 8B is an amplitude-time plot of a waveform with randomized pulse amplitude modulation.

FIG. 8B is an amplitude-time plot of a pulse-amplitude modulated (PAM) waveform 850, with randomized pulse amplitude (RPA). As shown in FIG. 8B, the amplitudes (A) of the individual pulses 810 vary according to a random or pseudorandom function, while the nominal pulse width W0 remains substantially constant; e.g., the "on" pulse width W0 may also be equal to the nominal width of the corresponding "off" pulse segment 815, as shown.

In the particular example of FIG. 8B, the nominal period T=T0 is substantially the same for each individual pulse 810 in the pulse-amplitude modulated waveform 850. Thus, the carrier frequency f=1/T0 is also substantially constant. In other applications, the pulse period and carrier frequency may vary, along with the number of pulses and individual pulse widths.

As shown in FIG. 8B, the amplitudes A=Ai, Aj of individual pulses 810 can vary with respect to the nominal value A=A0. Some pulses, for example, have a relatively lower amplitude Ai<A0, corresponding to a negative amplitude deviation $Di^{(-)}=-|A0-Ai|$. Other pulses have a relatively greater amplitude Aj>A0, with a positive deviation $Dj^{(+)}=+|Aj-A0|$. The amplitude modulation can be applied in the same sequence to each phase, so that the amplitudes Ai, Aj of the individual pules 610 are the same in the first (e.g., positive) phase 820 and the second (e.g., negative) phase 825, in the same order, or the amplitude modulations can be applied in any sequence, so that the individual pulse amplitudes Ai, Aj vary in each phase 820, 825, in any order.

The randomized modulating function applied to pulse-amplitude modulated (PAM) waveform 850 can be constrained so that the integrated pulse amplitude is constant over each successive pulse train or treatment phase 820, 825, in order to achieve charge and current balancing. Similarly, the modulation function can be constrained to deliver the same integrated power over successive phases 820 and 825, and so that the net integrated charge and current are substantially zero (or approach zero within a selected minimum of threshold value, as described above). Alternatively, the modulation function may be unconstrained, and the integrated amplitudes of any waveform 850 or other waveform described here may vary from pulse to pulse and from phase to phase, along with the applied voltage, current and power.

Figure 9:
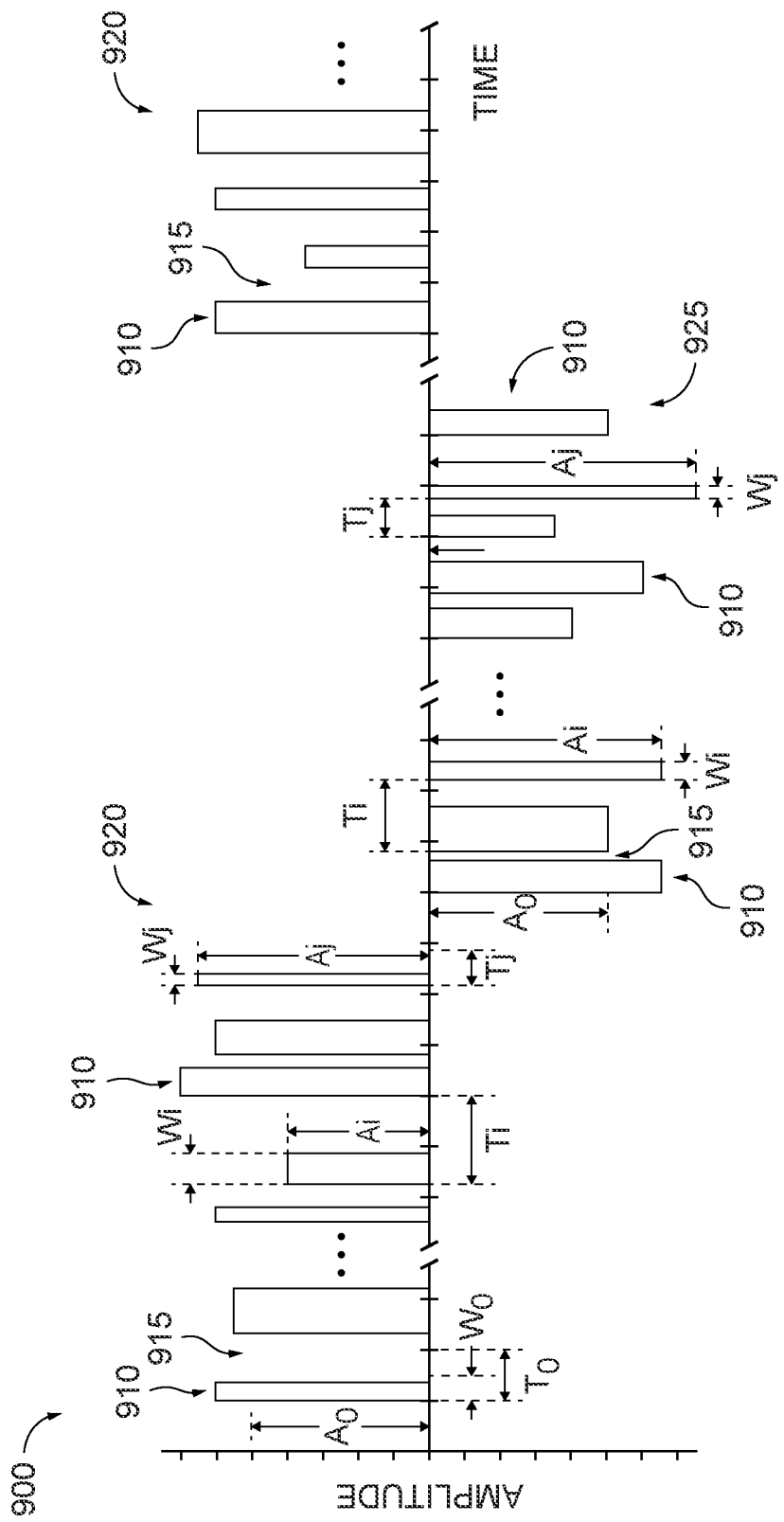
FIG. 9 is an amplitude-time plot of a waveform with randomized pulse-width, pulse frequency and pulse amplitude modulation.

FIG. 9 is an amplitude-time plot of a waveform 900 with a combination of randomized pulse-width (RPW) modulation, randomized pulse amplitude (RPA) modulation, and randomized pulse frequency (RPF) modulation. In this particular example, the pulse width (W) and amplitude (A) vary among the individual pulses 910, as well as the pulse period (T) and corresponding instantaneous carrier frequency f=1/T. The number of individual pulses (N) can also vary, as distributed among the successive (e.g., positive and negative polarity) phases 920 and 925.

As shown in FIG. 9, a randomized modulating function is applied to waveform 900 in order to vary the widths Wi, Wj of individual pulses 910 with respect to the nominal width W0. The modulation function can also be adapted to randomize the pulse amplitudes Ai, Aj, as defined with respect to the nominal value A0, and the instantaneous carrier frequency f=1/T, which varies according to the individual pulse periods Ti, Tj. The widths of the "off" pulse segments 915 may also vary, as the as defined with respect to the nominal "on" pulse width W0.

A single modulating function can be applied to randomize each of the selected pulse parameters, or a combination of modulating functions may be used. The modulation functions can also be adapted to maintain a fixed or constant pulse width, pulse amplitude, pulse period or frequency across the sequence of individual pulses 610 making up any one or more consecutive pulses 910, in the same order, or the modulations can be applied in any sequence, combination, or order. Similarly, the number of individual pulses (N) may be the same in each sequential phase 920, 925, or the number of pulses (N) may vary from phase to phase.

Suitable randomized modulating functions can be constrained to maintain a constant integrated pulse amplitude over each successive phase 920, 925, in order to achieve charge, current and power balance. The modulation function can also be constrained to maintain a constant application time window N×T0 in each phase 920, 925, so that successive phases are equally spaced in time. Alternatively, the modulation function can be unconstrained with respect to the total pulse width or integrated pulse amplitude, or both, and the applied stimuli will vary accordingly.

Randomized Pulse Modulation Functions

Figure 10:
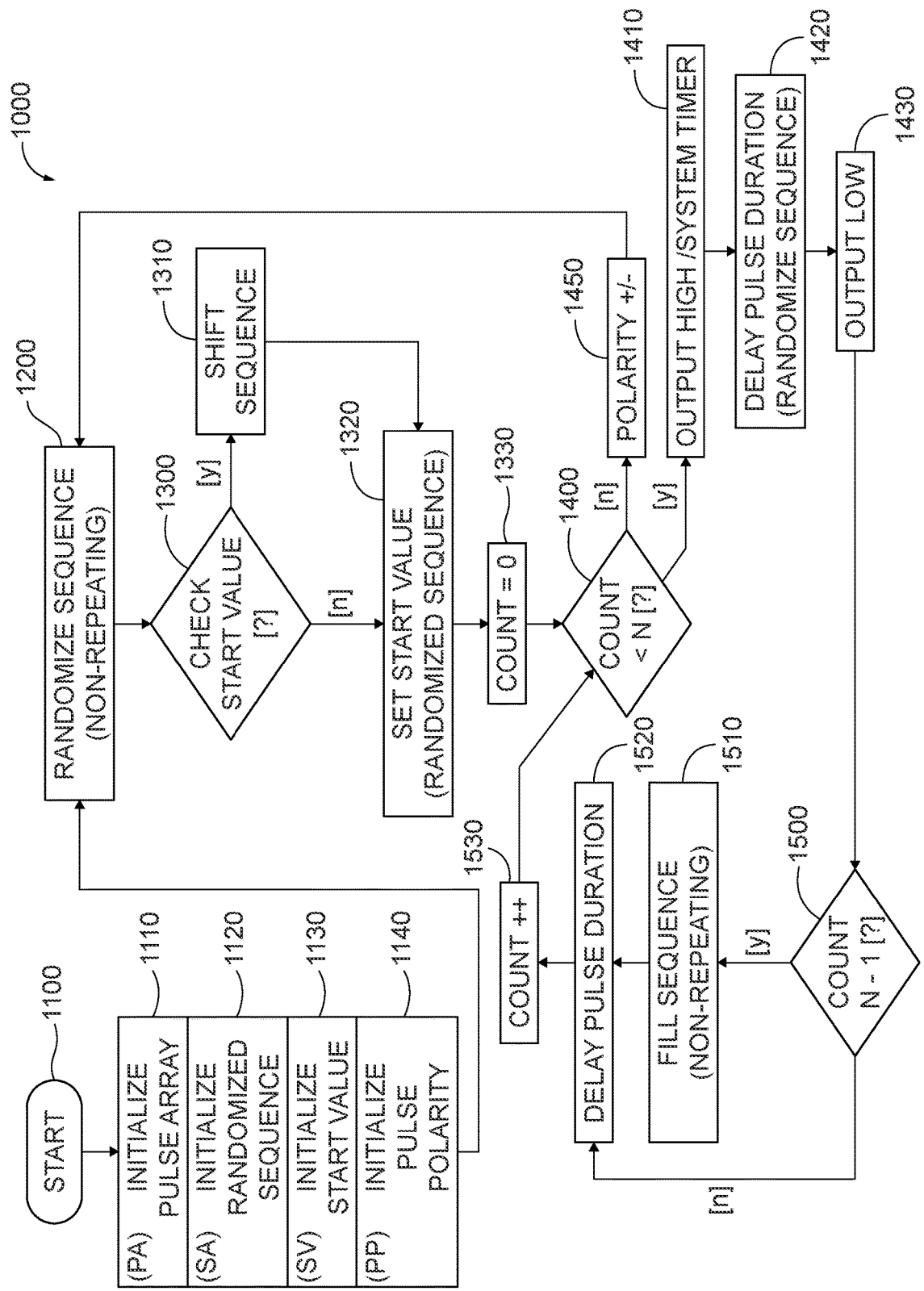
FIG. 10 is a block diagram of a function or process for randomized pulse width, pulse frequency and pulse amplitude modulation.

FIG. 10 is a block diagram of a modulating function or method 1000 for randomized pulse width modulation, suitable for use with any of the waveforms described herein. For example, the modulation function or method 1000 can be applied to modulate a waveform in order to apply an electrical stimulus with a device 300 as shown in FIG. 3, for microcurrent-based skin treatment according to method 400 of FIG. 4, or for pulsed waveform modulation according to method 500 of FIG. 5.

In the particular example of FIG. 10, modulation function or method 1000 includes one or more of a start block or process step 1100 with one or more initiation sub-functions or steps 1110, 1120, 1130 and 1140; a sequence randomization process block or step 1200; a start value process block or step 1300 with one or more shift, set and count sub-functions or steps 1310, 1320 and 1330; a pulse count block or step 1400 with one or more output, system timer, delay and polarity toggling sub-functions or steps 1410, 1420, 1430 and 1450; and a pulse increment process block or step 1500 with one or more sequence, delay, and count increment sub-functions or steps 1510, 1520 and 1530. These functions, sub-functions, process blocks and steps can be performed in any order or combination, with or without additional functions and techniques as described herein.

The function or method 1000 can be initiated at a start operation or step 1100. The associated initialization steps 1110, 1120, 1130 and 1140 can be executed as process steps or sub-functions, in order to generate an initial pulse parameter vector or array PA characterizing a set of N pulses in the waveform or phase (initialize pulse array step 1110), and to generate an initial randomized (or other non-repeating) sequence vector or array RA characterizing a sequence in which the pulses may appear (initialize randomized sequence step 1120).

The pulse parameter array PA characterizes the pulse width of individual pulses in the waveform, or any combination of pulse parameters including pulse width, period, frequency and amplitude. The pulse amplitude parameters can be randomized according to the sequence array RA, or the individual parameter values can be randomized so that they are aperiodic, or varied in some other random, pseudorandom, non-repeating, aperiodic or predefined fashion. Some of the pulse parameters may also be fixed or substantially constant, for example in order to vary the pulse width (or other pulse parameter) independently of the others.

To initialize a start value (step 1130), the start value vector or array SA is set to zero (or other suitable initial value), for example to reference a prior or preselected starting sequence, or an initial set of randomized waveform parameters. More generally, the start value array SA can either be used to track either the individual waveform modulation values in modulation parameter array PA, or the randomized array RA (or other random, pseudorandom, or predefined array) indicating the sequence in which the varying pulse parameters are applied, in order to modulate consecutive pulses in the waveform.

To initialize pulse polarity (step 1140), a pulse polarity indicator PP is generated or defined. For example, a bipolar polarity indicator PP may be defined to designate the positive or negative phase of a modulated pulse application, or a unipolar indicated PP may be defined to indicate one or more sequential unipolar phases.

In the sequence randomization block (randomize sequence step 1200), the array RA characterizing the waveform sequence (step 1120) is filled with a randomized set of different values, indicating the sequence in which the array of pulse modulation parameters PA should be applied to modulate the waveform. For example, a set of pseudorandom integer numbers may be used to randomize the sequence in a non-repeating manner, or another ordered, non-repeating, aperiodic set of variables can be used, corresponding to sequence of N pulses in a given phase. Alternatively, the array of pulse modulations parameters PA can be generated or regenerated with a random, pseudorandom, or other non-repeating or aperiodic component, and the sequence in which they are applied can remain the same, or both the sequence and the parameters themselves may be randomized.

In the check start value block (step 1300), the randomized sequence array RA or pulse parameter array PA is compared to a corresponding start value array SA. If the randomized sequence is the same as the start value (or if the modulation parameters are the same), the sequence array RA can be shifted (shift sequence step 1310) in order to avoid repeating the same sequence. Depending on application, the randomized sequence array RA can be cyclically shifted one or more positions in either direction, or otherwise reordered, in order to change the sequence in which the pulse modulation parameters in array PA are applied to consecutive pulses. Alternatively, one or both of the modulation parameters (array PA) and the sequence (array RA) can be regenerated with a new set of randomized, pseudorandom, or other non-repeating or aperiodic values; e.g., by returning operation to the randomize sequence step 1200.

If the randomized sequence array RA is not the same as the start value array SA (or after it has been shifted or re-sequenced), the start value array SA is reset to the current randomized sequence array RA (set start value step 1320). Similarly, if the applied pulse modulation parameter array PA is not the same as the corresponding start value (or after it has been-re-randomized), the start value array SA can be reset to the current parameter array PA.

Thus, the start value array SA can be used to track either the most recent sequence in which the modulated waveform parameters PA are applied, or the actual parameter values themselves (or both). One the start value is updated (step 1320), the pulse count is reset to zero (step 1330), and successive pulses in the waveform can be counted out as they are applied.

The pulse count is checked at the start of the pulse count block (step 1400). If the count has not reached the number of desired pulses (N) in the phase or waveform, the next pulse can be output according to steps 1410, 1420 and 1430. If the count has reached the number of pulses (N), the polarity indicator PP is switched (at toggle polarity +/− step 1450), before returning operation to the sequence randomization block (step 1200). For example, the polarity indicator PP can be toggled between positive and negative phases, or to indicate that a new phase is to be initiated in a unipolar application.

The waveform pulse is applied by setting the output high, and checking the system timer to determine the appropriate delay (step 1410). For example, a controller can be used to direct a voltage or current supply to apply a "high" or "on" signal to one or more electrodes, according to the desired pulse amplitude. The controller can also read or access the system clock or timer, in order to maintain the output amplitude for a delay time based on the desired pulse width or pulse duration (delay pulse duration step 1420).

The pulse width (and pulse frequency, period and amplitude) parameters used to modulate each successive pulse are determined from the pulse modulation parameter array PA, and applied in sequence to the consecutive pulses according to the randomized sequence array RA. Once the pulse has been output for the desired duration, the output is set to zero or other default "low" (or "off") value, at the output low step (block 1430).

The pulse count is checked again (step 1500), and, if the count has reached N−1, the random sequence array RA can be re-filled with pseudo-random integers or other ordered, non-repeating values, at fill sequence block (step 1510). Alternatively, the pulse parameter array PA can be reset with a new set of randomized, pseudorandom, or other non-repeating or aperiodic values (see randomize sequence step 1200).

At the delay pulse duration step (step 1520), the output low ("off") state is maintained for the desired duration, according the selected pulse width, period, or frequency parameter (delay pulse duration step 1520). Alternatively the pulse polarity can be reversed, in embodiments where bipolar pulses are applied.

The count is then incremented (count ++ step 1530), and the process returns to the check count block (step 1400). The function or method 1000 can then be iterated until the desired number of pulses N has been applied in each polarity phase, and until the desired number of treatment phases are applied, or until the process is manually stopped (e.g., by the user).

Representative Device Embodiments

Figure 11A:
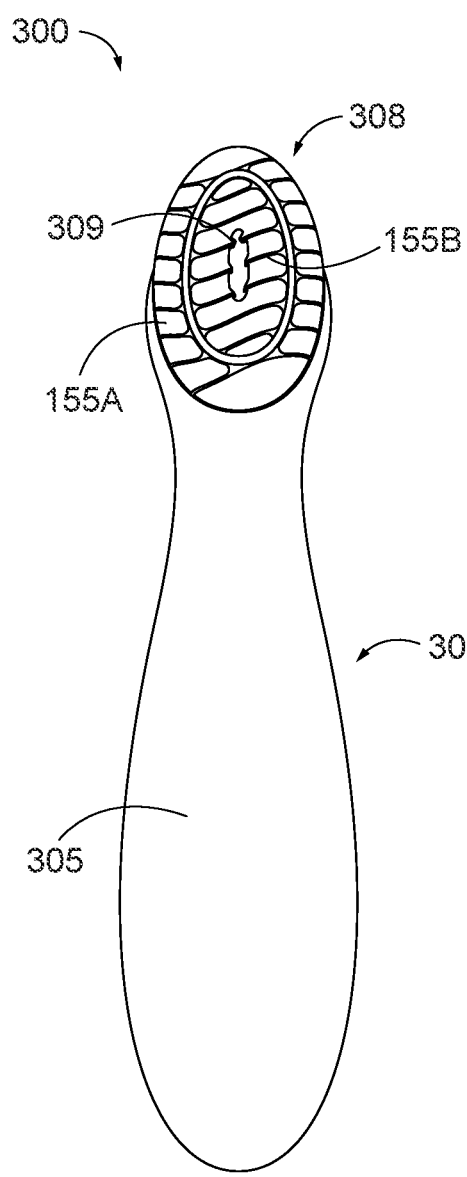
FIG. 11A is a front view of one embodiment of a handheld device for generating and applying modulated waveform stimuli, as described herein.
Figure 11B:
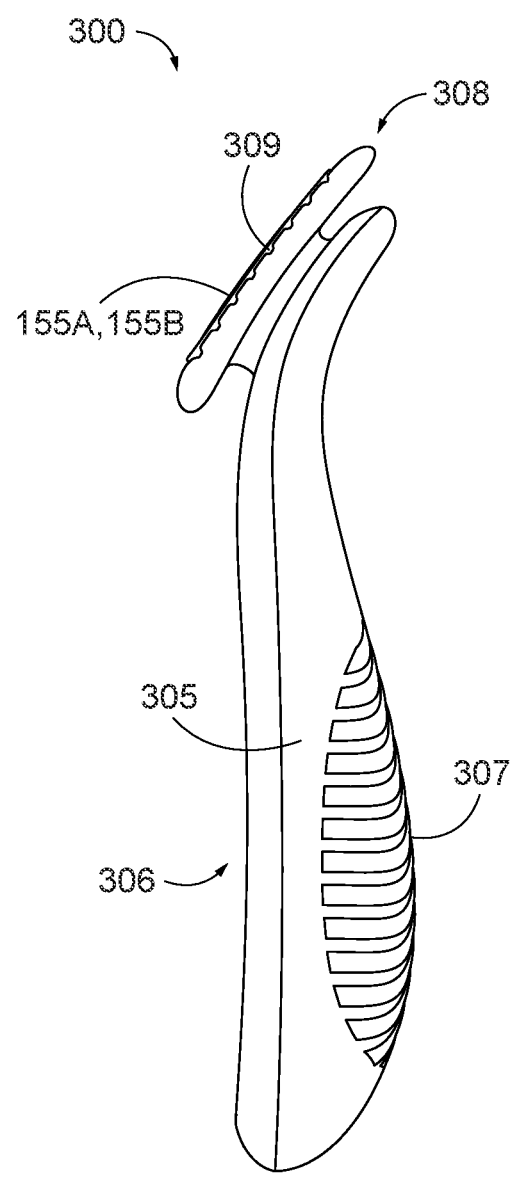
FIG. 11B is a side view of the device in FIG. 11A.

FIGS. 11A and 11B are front and side external views, respectively, showing embodiments of a representative skin treatment device 300 within a hand-held housing 305. The housing 305 can be configured for enclosing a power supply 310 with a voltage or current generator (or source) 320, as well as a microprocessor controller 330, memory 340, user interface 350 and other internal components; e.g., as described above with respect to FIG. 3.

As can be seen in the particular embodiments of FIGS. 11A and 11B, the elongated housing 305 can include a handle 306; e.g., with a textured gripping area 307 and a skin contact head 308 formed at its upper end. The skin contact head 308 is shown as having at its outer face one, two or more electrodes 155A, 155B; e.g., with conductive surfaces that can be textured with a pattern to generate an electric stimulus or other energetic stimulus 150; e.g., a microcurrent stimulus for delivery to a subject's skin. Suitable surface patterns are described, for example, in U.S. Design patent application No. 29/732,120, MICROCURRENT SKIN TREATMENT DEVICE, filed Apr. 21, 2020, which is incorporated by reference herein, in the entirety and for all purposes.

In these particular examples, an outer electrode 155A is formed generally as an elliptical band that follows the outer periphery of the head 308 and encloses an elliptically shaped inner electrode 155B. In the center of electrode 155B is an area 309 that may contain one or more skin sensors and other environmental sensors 158; e.g., as described above.

Biological Effects

The use of programmed, randomized pulse width modulation (PRPWM) can have a variety of different biological effects, when the modulated waveform is applied as an electrical (e.g., voltage or current) stimulus to a subject's skin. These applications are distinct from those using an unmodulated or "un-randomized" (periodic or repeating) waveform, where the pulse width, pulse amplitude and pulse period may not vary from pulse to pulse, or across the individual pulses within a given treatment phase.

The beneficial effects of microcurrent skin stimulation using randomized pulse waveform modulation depend upon the applied stimulus. Generally, the microcurrent treatments disclosed here are insufficient to substantially increase skin temperature by resistive heating, or to induce directly electrochemical reactions or nerve and muscle stimulation, due to the low levels of applied voltage, current and charge. Other effects, however, may have both biological and electrochemical aspects. The benefits, moreover, are not necessary limited to cutaneous tissues in the skin itself, and may also extend to include the underlying subcutaneous layer. These effects may include, but are not limited to, changes in tissue resistivity, circulatory blood flow, connective tissue and collagen properties, and ATP (adenosine triphosphate) synthesis and amino acid uptake.

It is also well-established that electrical stimulation can change selected properties of skin tissue, which in turn can be characterized by changes in resistivity. For these effects, a few minutes of microcurrent stimulation can be sufficient to elicit desired changes, when applied within the voltage, current and power ranges disclosed here. Since the disclosed devices and methods can be applied in a unipolar or bipolar mode, moreover, these effects may be responsive both to the net charge, current or power applied in each treatment phase, and to the total charge, current and power applied over a complete treatment cycle.

For example, studies have confirmed increases in circulatory blood responsive to microcurrent stimulation, including treatments using an electrolyte solution or other treatment product applied topically to the skin. Increased circulation, in turn, has been linked to other beneficial biological effects, including improvements in capillary formation, healing, and nerve function.

Microcurrent skin treatments can also enhance the formation and regeneration of collagen and other connective tissues; e.g., in the epidermal, dermal, and subcutaneous tissue layers. Substantial results may also be seen after repeated treatment cycles, for example once or more daily, over a period of a few to several weeks or months. Studies have also shown that accelerated healing responsive to microcurrent therapies with alternating (reversed) positive and negative polarity phases, as disclosed here.

Microcurrent skin treatments have also been shown to enhance rates of cellular ATP production and amino acid uptake. The associated increases in cellular metabolism and protein synthesis rates may be related to enhanced collagen formation, as described above, and these benefits may accrue over treatment periods of a few weeks or more, with integrated treatment cycle times approaching two or more hours.

As explained above, the skin's response to an electrical stimulus depends on both the net charge or current delivered per treatment phase, and the total charge or current delivered over a full treatment cycle, including a number of sequential phases having the same or opposite polarity. The tendency for homeostasis may reduce the skin's response, however, when subject to a more constant or strictly periodic stimulus. Such a stimulus may also cause tissue to develop a corresponding periodic response to preserve a state of homeostasis in the skin tissue, which the body senses is being disrupted. Modulating the electrical pulses that are applied to the skin with a random or pseudorandom component makes the pulses aperiodic, and randomized pulse width, amplitude, and period modulation may reduce the tendency for homeostasis or preservation of homeostasis. The beneficial effects may also be manifested by changes in resistivity, circulation, and ATP synthesis, which can in turn may benefit collagen formation and connective tissue properties.

The inventive systems and techniques disclosed here are amendable to different modifications and alternative forms. Specific applications are described by way of examples, and described in detail. Practice of the invention, however, is not limited to these particular examples and embodiments, and the scope of the invention includes any and all modifications, equivalents, and alternatives falling within the scope of the invention as claimed. In these various embodiments, the invention comprises any suitable combination of the elements described herein, and as recited in the claims, and the claims can be practiced in the absence of any element which is not specifically recited therein.

Other Energetic Stimuli

The general principle of providing an electrical stimulus to skin as described above can be extended to other energetic stimuli presented not only in an electrical form but also in other forms, in which energy may be presented to skin as a stimulus, such that the energy enters the skin tissue and can have biological effects. One example is the use of LEDs, low-power lasers or other emitters of electromagnetic radiation, generally called light, but which may also include or be presented as radio-frequency (RF), infrared (IR) or optical energy, or low-energy (near-UV) or other suitable ultraviolet (UV) light, or other visible or non-visible forms of light energy, from any suitable parts of the electromagnetic spectrum. Similarly, the stimulus can be provided in the form of acoustic energy, for example as subsonic, sonic, or ultrasonic stimulus. These various energetic stimuli are producible from an emitter, which is controllable to produce a modulated waveform with beneficial effects on the skin.

Such a controllable waveform can be modulated or controlled by causing one or more parameters of the waveform to be randomized or pseudo-randomized, as described herein. To the extent these modulation and controlled modulation and randomization techniques discussed above can be applied to electrical stimuli to project energy into skin with beneficial effects, the same or similar techniques can be applied to other energetic stimuli including, but not limited to, electromagnetic and acoustic stimuli, or any combination thereof. Thus, the principles discussed here can be applied in analogous manner by modulating a set of consecutive pulses in other energetic waveforms, where pulse widths of the consecutive pulses vary in a random or pseudorandom fashion.

These applications open up options for skin treatment in which other or additional biological processes in the skin are beneficially affected by introducing a suitable (e.g., low-level) energetic stimulus using the same or analogous waveform modulation techniques for the energetic stimuli transmitted to the skin from one or more emitters. For the reasons stated above, these other stimuli can also produce beneficial effects, and can be introduced to the skin to affect these and other biological processes.

For example, with respect to LED lights or other light energy directed to skin, the light or other electromagnetic energy output of the emitters can be presented in pulses, where the pulse width, period, frequency or amplitude of the consecutive pulses varies in a random, pseudorandom, or other aperiodic manner. Accordingly, the waveform control and modulation techniques described above are equally applicable to electrical, electromagnetic, and acoustic stimuli that involve voltage, current, light, sound and other forms of energetic stimuli, and combinations thereof, which can be generated, emitted and transmitted in a relatively focused manner onto, into, or through a limited skin area, or other suitable area of the skin selected for treatment.

Experimental Data

The following examples describe experiments designed and performed to provide information on the efficacy and/or utility of the devices and methods described herein. In each example described here, references to an ageLOC LumiSpa Microcurrent Attachment device with PRPWM refer to such a device disclosed by the present disclosure, for example a microcurrent device with PRPWM, a microcurrent attachment with PRPWM, or a PRPWM microcurrent device, as described herein.

All of these examples were selected using appropriate inclusion and exclusion criteria, and are merely representative. Other examples and embodiments also exist, as described by the present disclosure, and as defined within the scope of the appended claims.

EXAMPLE 1: Four-Week Clinical Study Using Microcurrent with PRPWM. The objective of this research was to observe and understand tolerability, use, comfort, and beneficial skin appearance efficacy associated with the use of a microcurrent device with PRPWM and a conductive gel containing: water (aqua), glycerin, pentylene glycol, carbomer, sodium hydroxide, and chlorphenesin, as compared to a control where the same conductive gel was applied but no microcurrent device was used.

The methodology was a Split-face study design. Subjects who met all of the inclusion criteria and none of the exclusion criteria and also who have not used any anti-aging treatment skin care products were invited to the research center. Twenty subjects completed the evaluation. They were females, with skin types ranging from Fitzpatrick I-III, 25-40 years old. A Conductive Gel available from Nu Skin Enterprises, Inc. of Provo, Utah and having the above ingredients was applied to the whole face of each subject. An ageLOC LumiSpa Microcurrent Attachment device with PRPWM was used on one randomly-selected side of the face during a four-week period. The use instructions were: Once daily, apply the gel to the entire face. Use the device on the face, only on the one randomized side of the face, for 1 minute. Use of gel on both sides of the face prevents the gel itself from being a differentiating factor.

Following enrollment, subjects used the conductive gel over the entire face, but used the device on one randomized side of the face. The investigator and subjects assessed skin appearance on both sides and tolerability to provide a baseline value for comparison. A questionnaire was completed. Subjects were given a compliance diary and told to use the device as stated above. They were instructed on how to use the device and used the device for the first time at the research center under staff supervision.

Post-first application, the investigator and subjects assessed the subjects' facial skin separately for each (PRPWM treated and untreated) side of the face for device efficacy and tolerability. The following timepoints were defined: Baseline, Post-Application, and weeks 1, 2, and 4.

Subjects were asked to return and did return to the research center at weeks 1, 2 and 4. Evaluations were completed at each timepoint: one by a clinical grader and the other by the subject's self-perception. The efficacy evaluations were done with a focus on multiple defined points of evaluation, including: tactile roughness, visual smoothness, global firmness, eye firmness, plumping, texture, fine lines, wrinkles, crow's feet, smile lines, cheek wrinkles, pigmentation, skin tone, jaw line contour, pores, radiance and overall.

The assessments were made on a 5 point scale: 0=none, 1=minimal, 2=mild, 3=moderate, 4=severe. The tolerability evaluations were made in terms of irritation, stinging, burning, itching, peeling, and dryness. The assessments were made on a 5 point scale: 0=none, 1=minimal, 2=mild, 3=moderate, 4=severe. The compliance diaries of subjects were checked at the evaluation timepoints.

Figure 12A:
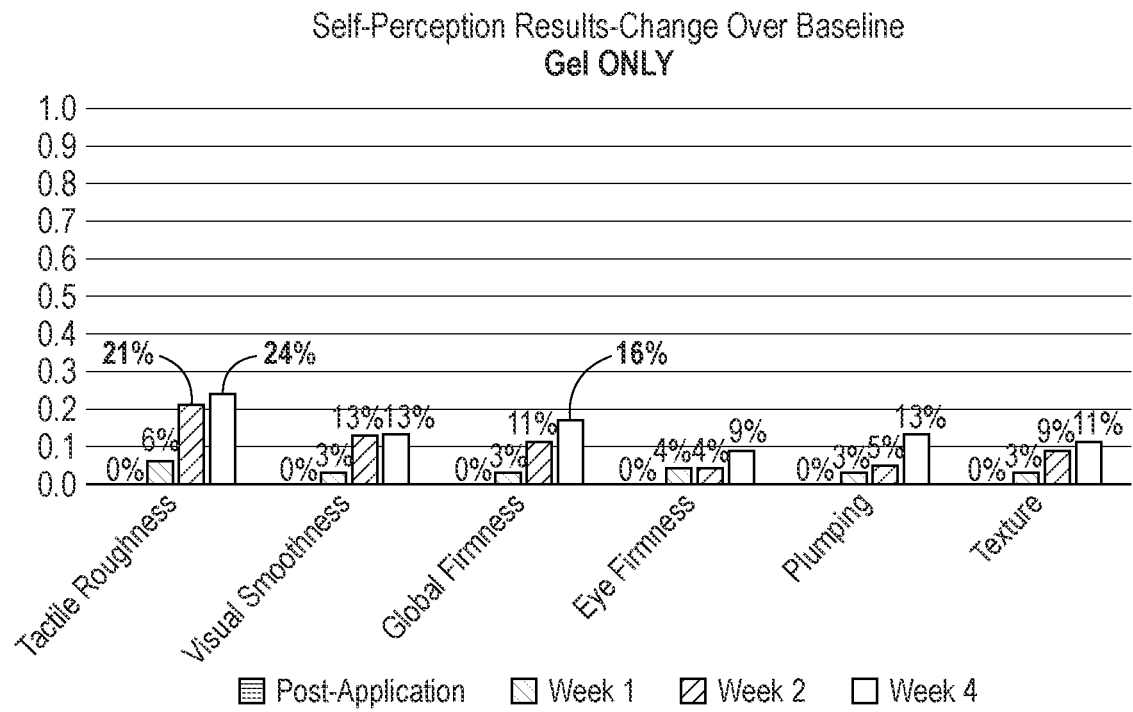
FIGS. 12A and 12B are bar graphs illustrating results from exemplary applications of a device for generating modulated waveform stimuli, as described herein, according to user self-evaluations for a first set of treatment criteria.
Figure 12B:
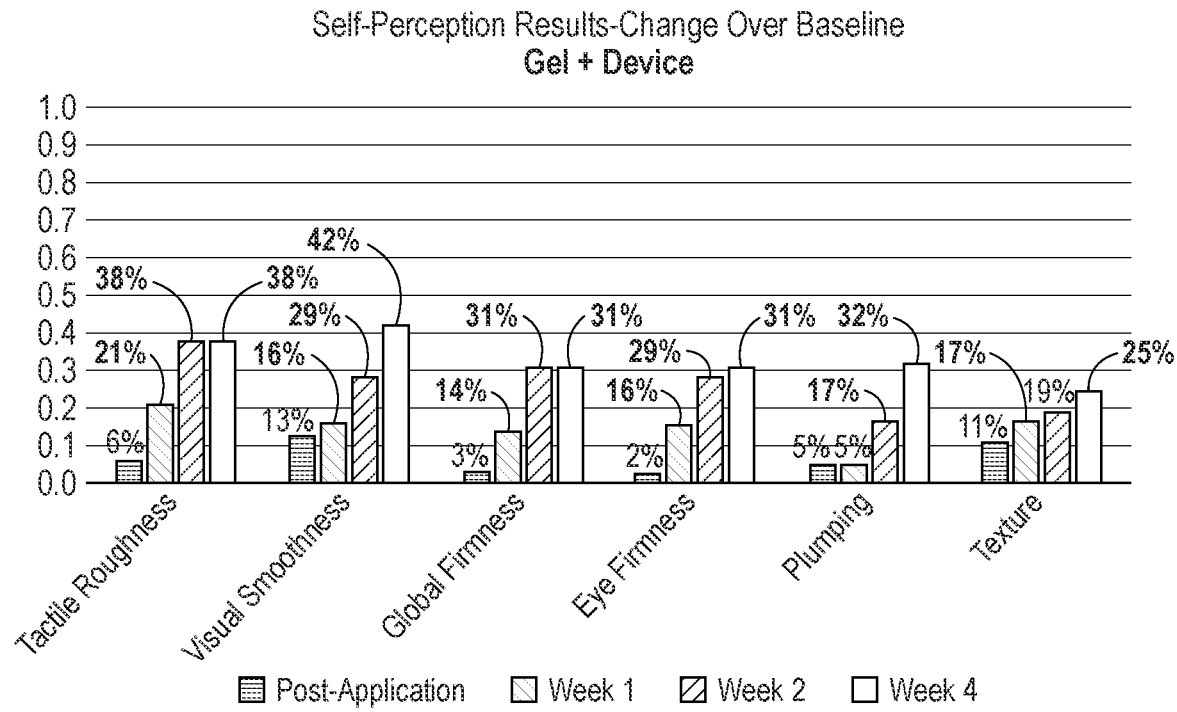

FIGS. 12A and 12B illustrate user self-perception results in percent change over baseline for a first set of skin treatment criteria (tactile roughness, visual smoothness, global firmness, eye firmness, plumping, and texture). Results are shown at post-application, and at week 1, 2 and 4 timepoints, respectively, for skin receiving a treatment gel only (FIG. 12A), and for skin receiving the gel plus a PRPWM microcurrent device treatment, as described herein (FIG. 12B).

Figure 12C:
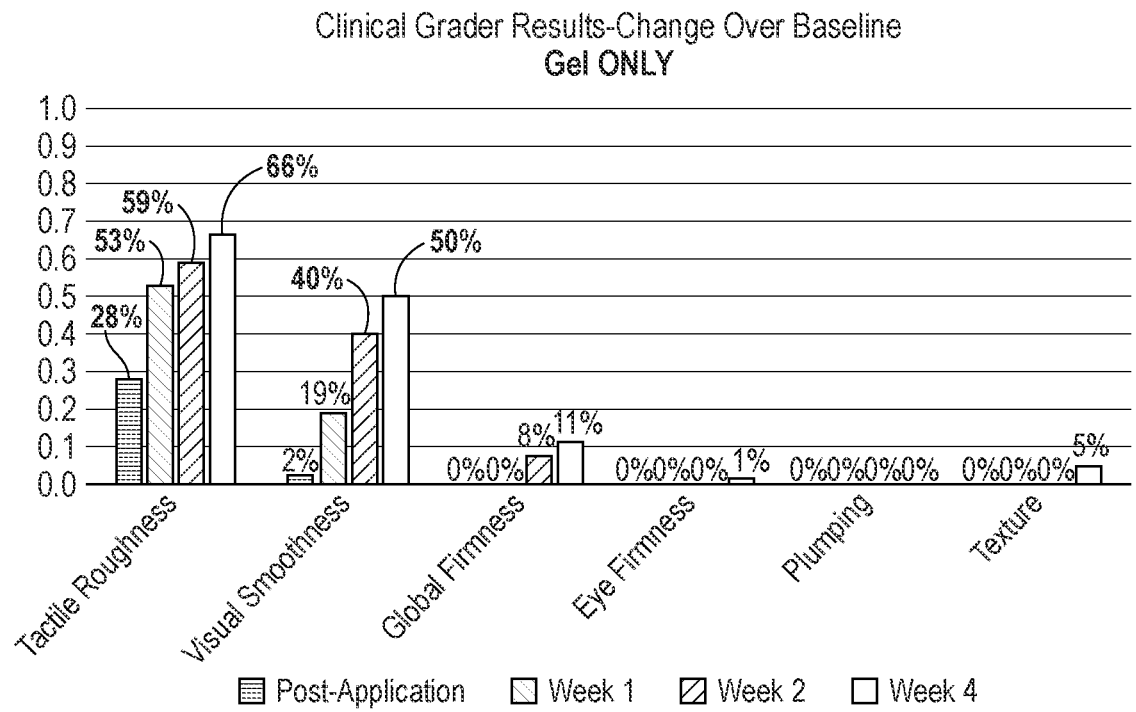
FIGS. 12C and 12D are bar graphs illustrating results for the first set of criteria, according to a clinical grader.
Figure 12D:
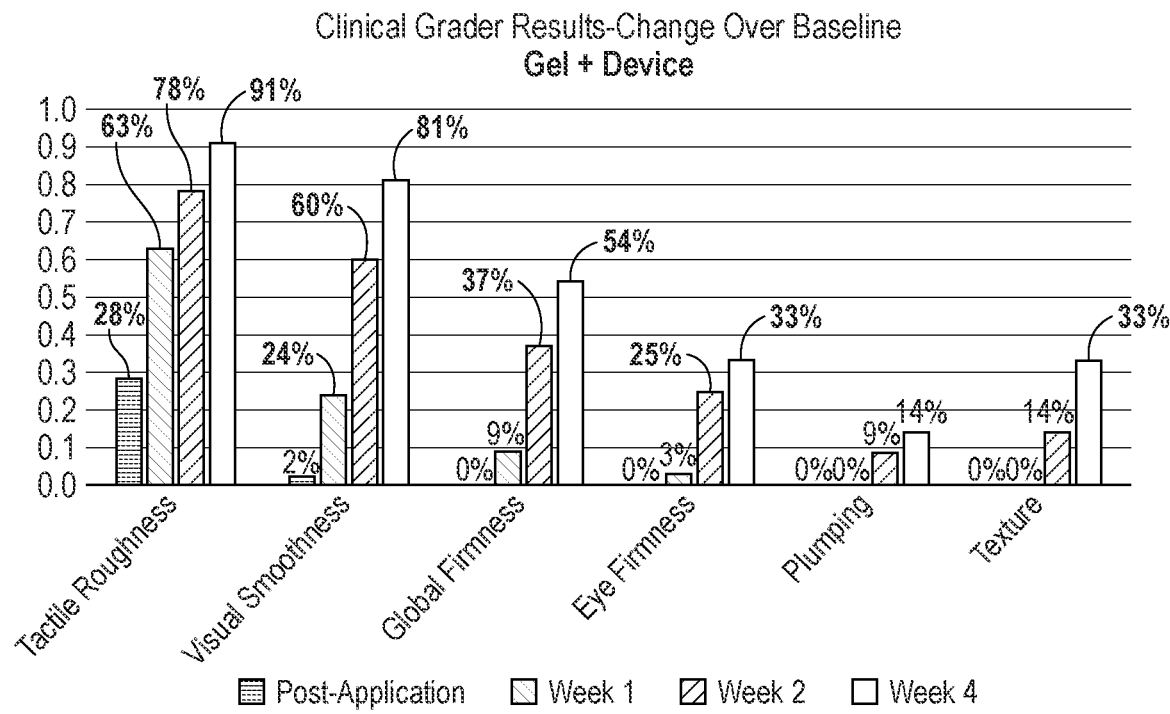

FIGS. 12C and 12D illustrate clinical grader results in percent change over baseline for the first set of criteria, at each of the respective timepoints. The results are shown for skin receiving the treatment gel only (FIG. 12C), as compared to skin receiving the gel plus a PRPWM device treatment (FIG. 12D).

In FIGS. 12A-12D, each group of four adjacent bars represents the change from baseline in one of the first set of criteria, for the timepoints at post-application and weeks 1, 2, and 4, respectively (bars running from left to right). Percentages above a bar indicate a change of statistical significance over the baseline, as determined for the respective treatment criterion and timepoint that the bar represents. Results for some criteria may indicate a greater effect based on user self-evaluation, at a given timepoint, while results for other criteria may indicate a greater effect based on clinical grading. Some results may also indicate that no substantial change was noted, based on either self-evaluation or clinical grading, rather than no observations having been made.

Figure 13A:
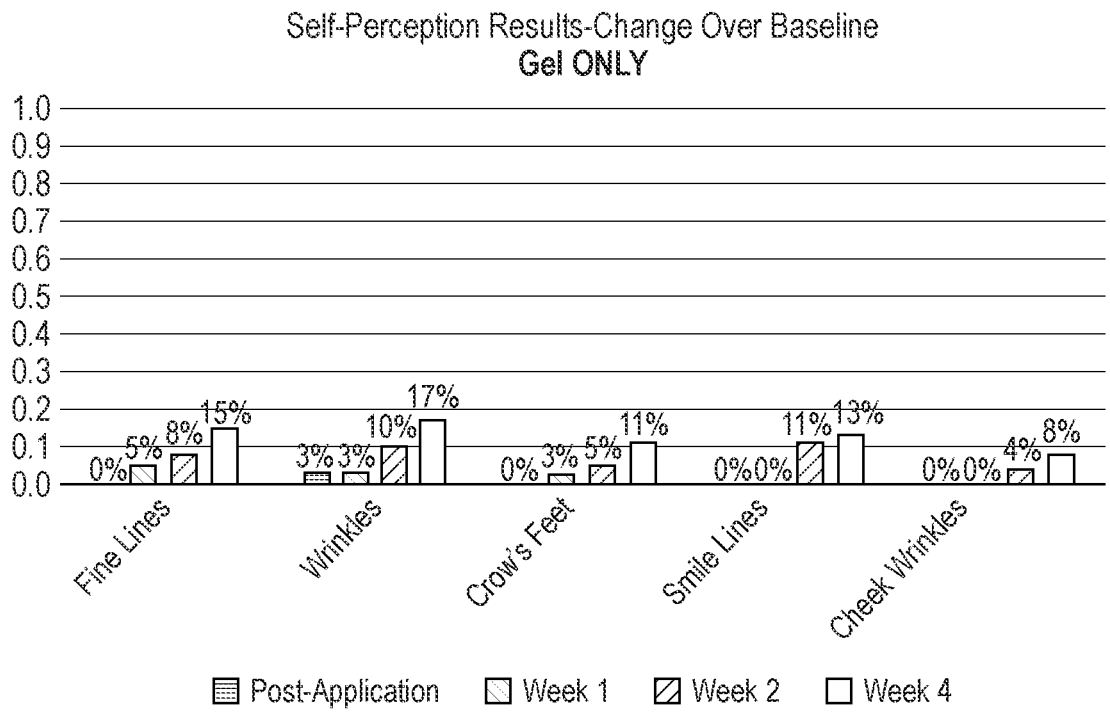
FIGS. 13A and 13B are bar graphs illustrating results from an exemplary applications of a device for generating modulated waveform stimuli, as described herein, according to user self-evaluations for a second set of treatment criteria.
Figure 13B:
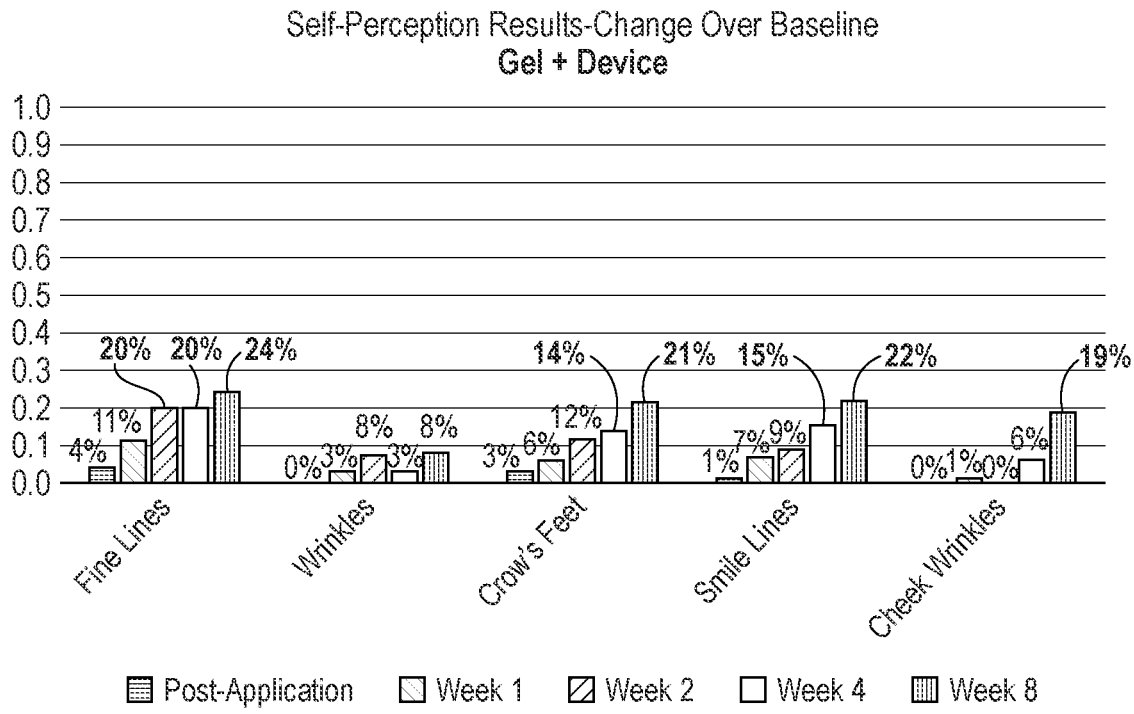

FIGS. 13A and 13B illustrate user self-perception results in percent change over baseline for a second set of skin treatment criteria (fine lines, wrinkles, crow's feet, smile lines, and cheek wrinkles). Results are shown at post-application and week 1, 2 and 4 timepoints, respectively, for skin receiving a treatment gel only (FIG. 13A), and for skin receiving the gel plus a PRPWM microcurrent device treatment, as described herein (FIG. 13B).

Figure 13C:
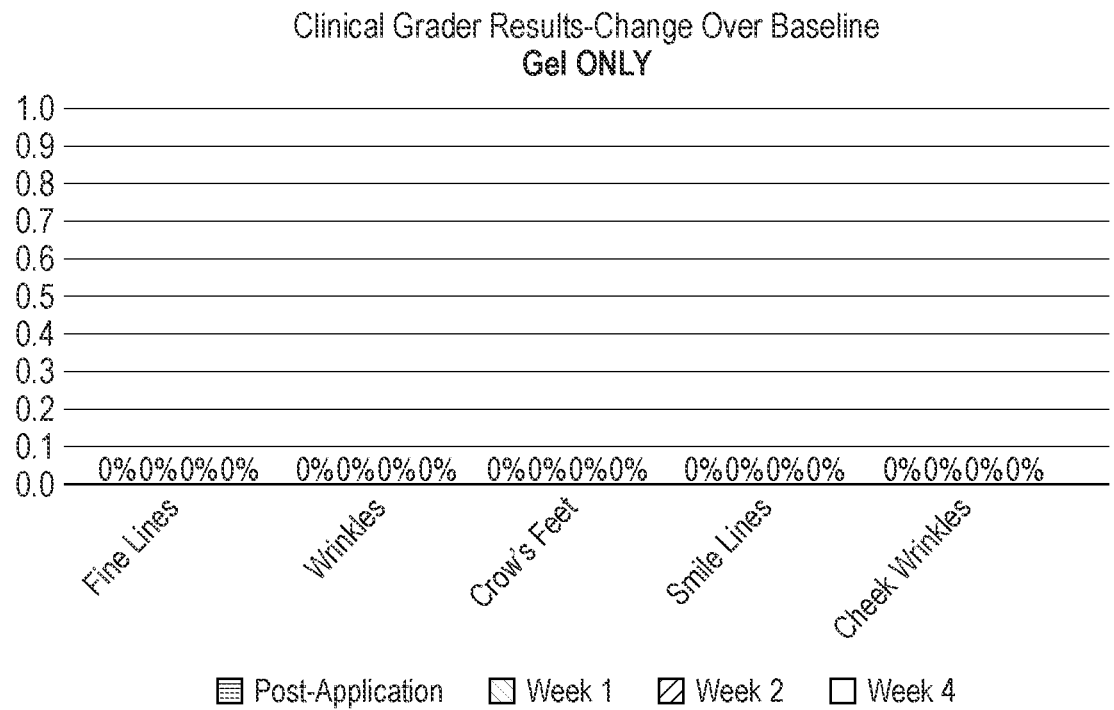
FIGS. 13C and 13D are bar graphs illustrating results for the second set of criteria, according to a clinical grader.
Figure 13D:
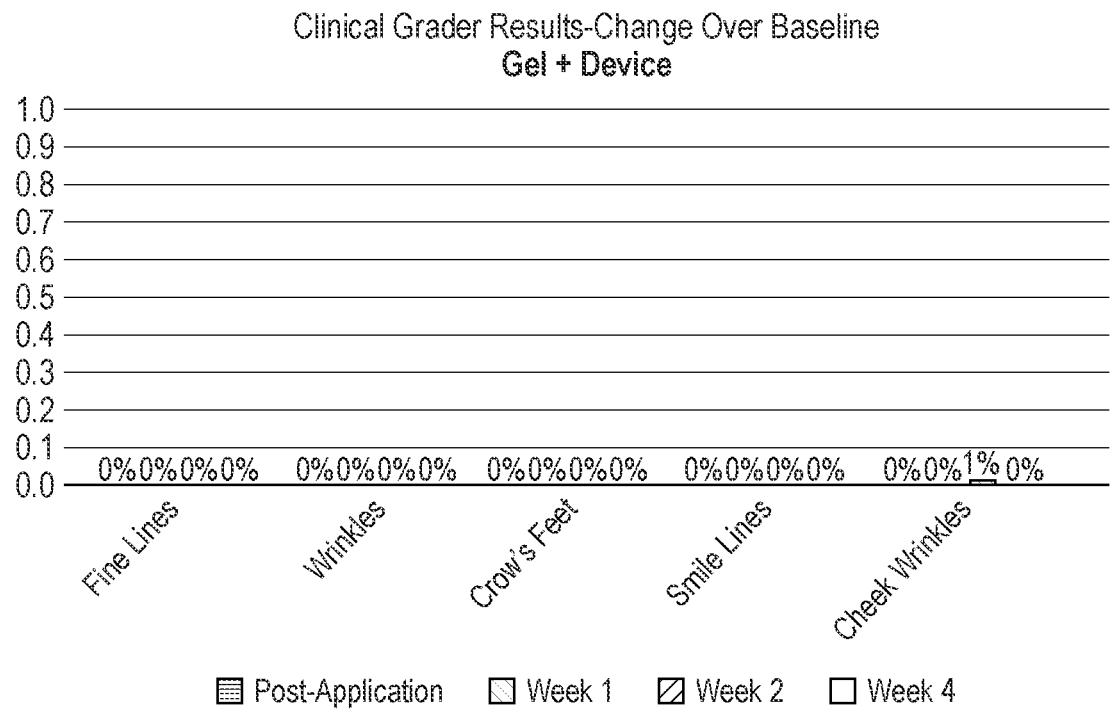

FIGS. 13C and 13D illustrate clinical grader results in percent change over baseline for the second set of criteria, at each of the respective timepoints. The results are shown for skin receiving the gel only (FIG. 13C), as compared to skin receiving the gel plus a PRPWM device treatment (FIG. 13D).

In FIGS. 13A-13D, each group of four adjacent bars represents the change from baseline in one of the second set of criteria, for the consecutive timepoints. In one example, data are also shown for an additional timepoint at week 8. Percentages indicate a change of statistical significance over the baseline, as determined for the respective treatment criterion and timepoint. Some results may indicate that no substantial change was noted, either for self-evaluation or clinical grading, rather than no observations having been made.

Figure 14A:
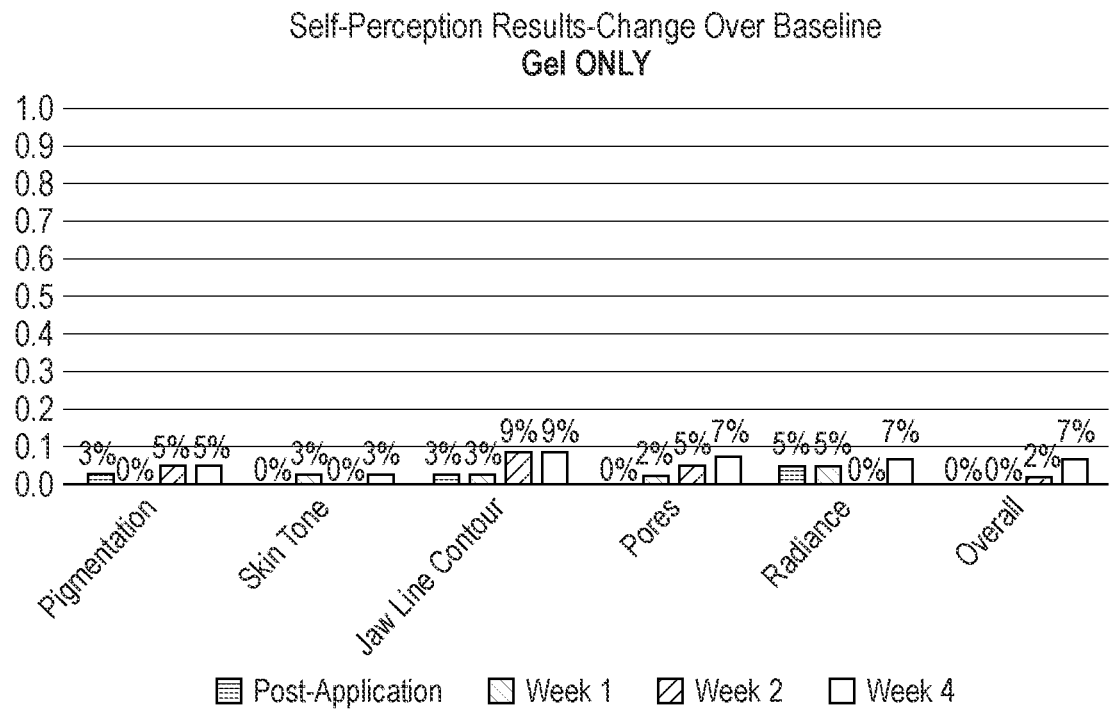
FIGS. 14A and 14B are bar graphs illustrating results from exemplary applications of a device for generating modulated waveform stimuli, as described herein, according to user self-evaluations for a third set of treatment criteria.
Figure 14B:
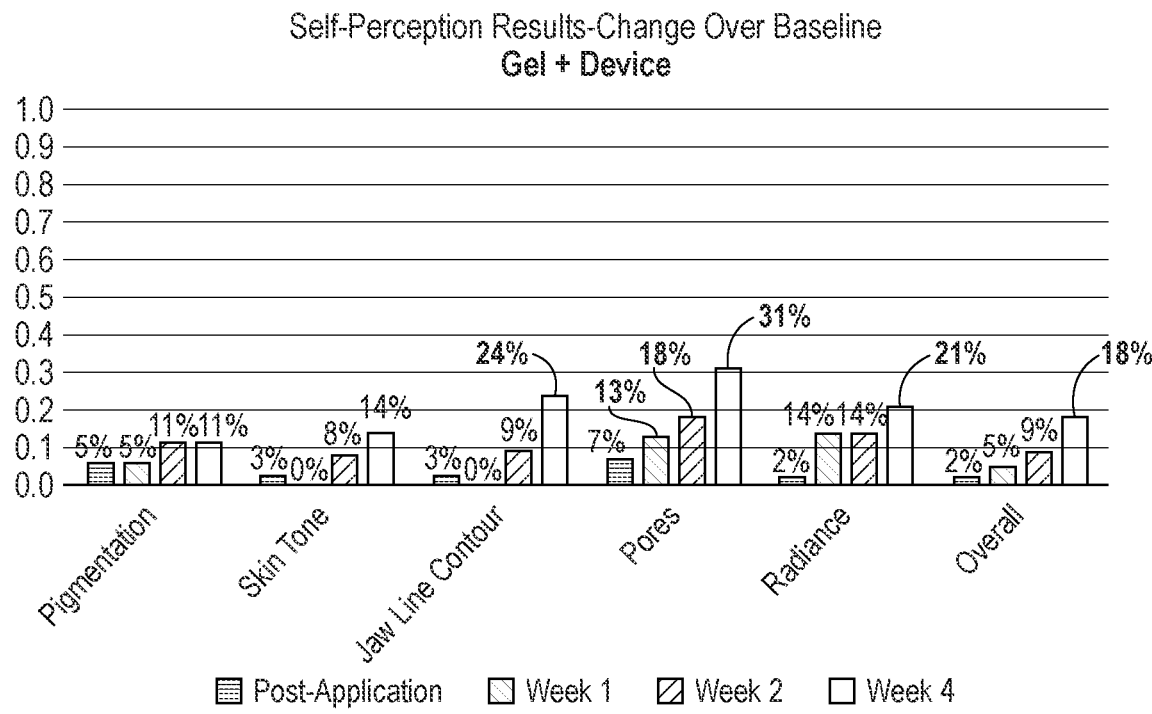

FIGS. 14A and 14B illustrate user self-perception results in percent change over baseline for third set of skin treatment criteria (pigmentation, skin tone, jaw line contour, pores, radiance, and overall appearance). Results are shown at post-application and week 1, 2 and 4 timepoints, respectively, for skin receiving a treatment gel only (FIG. 14A), and for skin receiving the gel plus a PRPWM device treatment, as described herein (FIG. 14B).

Figure 14C:
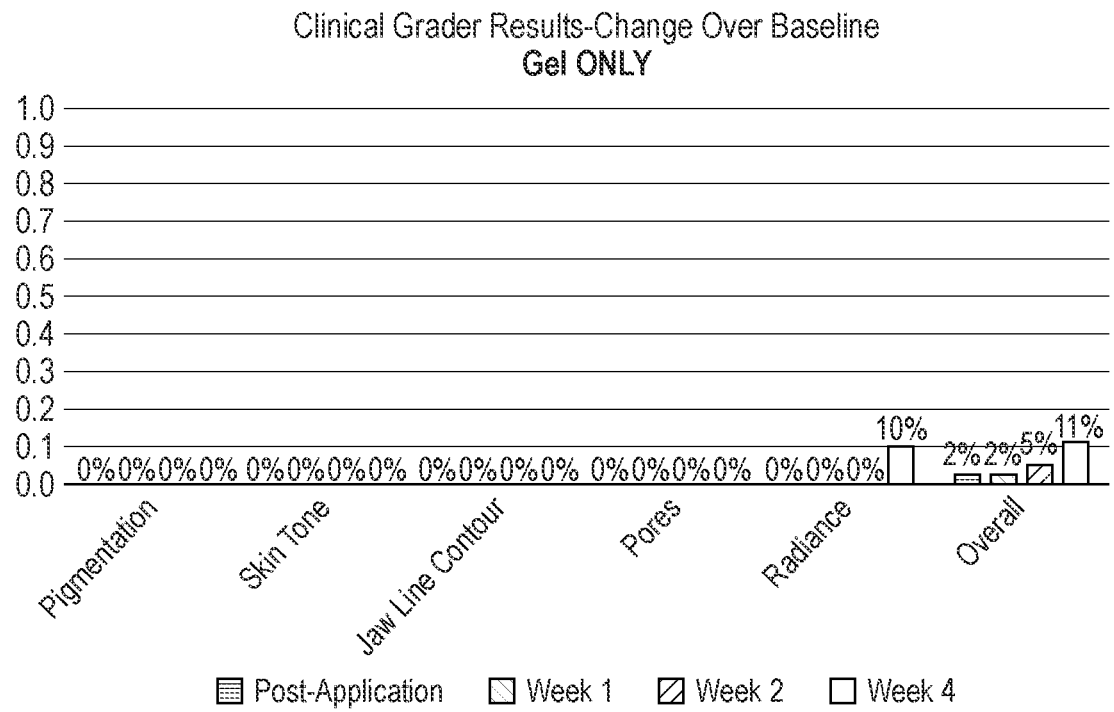
FIGS. 14C and 14D are bar graphs illustrating results for the third set of criteria, according to a clinical grader.
Figure 14D:
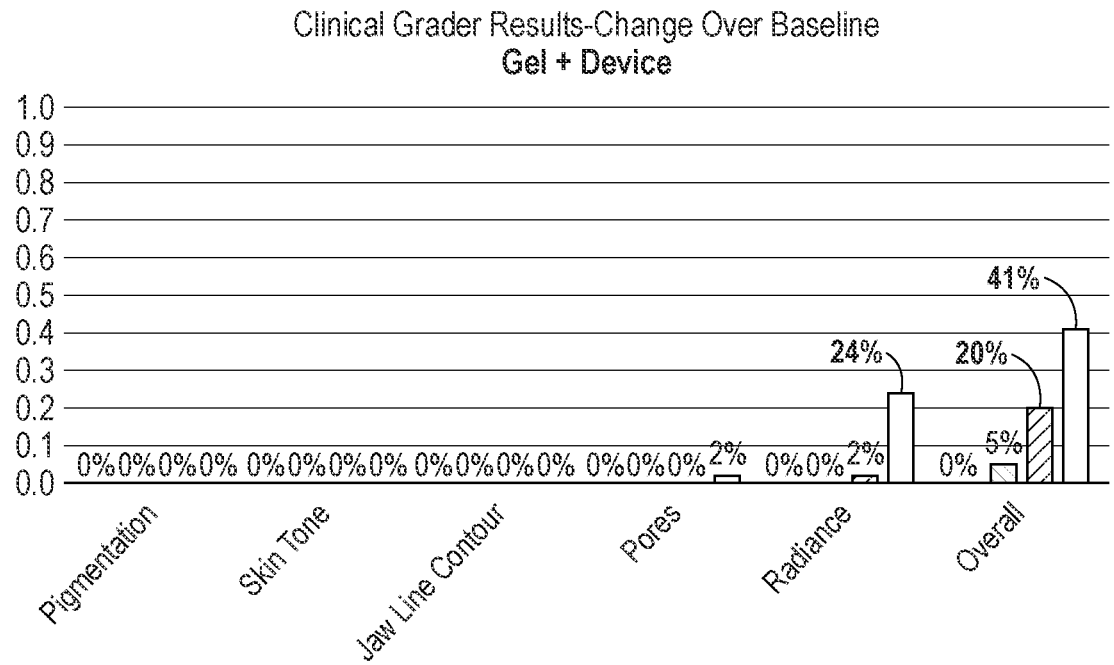

FIGS. 14C and 14D show clinical grader results in percent change over baseline for the third set of criteria (pigmentation, skin tone, jaw line contour, pores, radiance, and overall appearance), at each of the post-application, week 1, 2 and 4 timepoints. The results are shown for skin receiving the gel only (FIG. 14C), with comparison to skin receiving the gel plus the PRPWM device treatment (FIG. 14D).

In FIGS. 14A-14D, each group of four adjacent bars represents the change from baseline in one of the third set of criteria, for consecutive timepoints. Percentages a change of indicate statistical significance over the baseline, as determined for the respective treatment criterion and timepoint. Some criteria may exhibit a greater or lesser effect based on either user self-evaluation or clinical grading, and other results may indicate that no substantial change was noted (rather than no observations having been made).

Investigator Efficacy Assessment. The (blinded) investigator assessed the treated and untreated sides of the face separately. The difference vs. baseline analysis was identified as useful. Immediately after one use, both sides of the face generally demonstrated a reduction in roughness (FIGS. 12A-12D). This immediate effect could be due to the microcurrent gel that was used on both sides of the face, the microcurrent treatment, or both. The improvement in roughness on both sides of the face continued throughout the four weeks of the study.

At week 1, no statistically significant differences were observed between the treated and untreated sides of the face, at least for the first and second sets of criteria (e.g., as shown by boldface data and/or reference lines in FIGS. 12A-12D, 13A-13D and 14A-D). By week 2, there was statistically significant improvement in general facial firmness ($p=0.004$), eye firmness ($p=0.001$), and overall facial appearance ($p=0.031$) in the treated versus the untreated facial side (first and third sets of criteria, FIGS. 12A-12D and 14A-14D). These improvements continued into week 4, with a statistically significant improvement in roughness ($p=0.039$), smoothness ($p=0.019$), facial firmness ($p<0.001$), eye firmness ($p<0.001$), plumping ($p=0.024$), texture ($p=0.013$), and overall facial appearance ($p=0.001$). Accounting for the young age of the subject population, as specified by the sponsor, the subjects noted important improvement in firmness and skin visual and tactile characteristics after four weeks of device use.

Subject Efficacy Assessment. Generally, the (unblinded) subjects did not note any statistically significant changes immediately after one device use. At week 1, statistically significant improvement was noted by the subjects on the treated side of the face, in pore size ($p=0.046$) and radiance ($p=0.036$) (third set of criteria, FIGS. 14A-14D). The week 2 subject assessments demonstrated statistically significant improvement in eye firmness ($p=0.006$) (first set of criteria, FIGS. 12A-12D). By week 4, other additional assessments became statistically significant, including smoothness ($p=0.014$), eye firmness ($p=0.037$), and pore size ($p=0.008$) (first and third sets of criteria, FIGS. 12A-12D and 14A-14D).

The following represented efficacy endpoints:
  Primary Efficacy Endpoint: The primary efficacy endpoint was the ability of the microcurrent device to provide skin benefits compared to control as assessed by the investigator. The primary endpoint was met.
  Secondary Efficacy Endpoint: The secondary efficacy endpoint was the ability of the microcurrent device to provide skin benefits compared to control as assessed by the subjects. The secondary endpoint was met.
  Tolerability. No serious adverse events, adverse events, or adverse experiences occurred during the conduct of the study, per subjects and investigators. The safety endpoint was the absence of significant adverse reactions. All subjects met the safety endpoint. No skin problems occurred with use of the device as assessed by the investigator or the subjects.

EXAMPLE 2: Circulation/Bloodflow Procedures, Female Subjects. This was a one-day clinical study in healthy female volunteers to compare the effects on circulation/blood flow when using a microcurrent device with PRPWM along with a conductive gel and an investigation topical compared to baseline. The device used was the AgeLOC LumiSpa Microcurrent Attachment with PRPWM. The topicals used were: Nu Skin Conductive Gel (ingredients described above in Example 1), and an investigational formulation called MC Boost "East" (ingredients: water, glycerin, butylene glycol, dimethicone, niacinamide, tetrahexyldecyl ascorbate, polyglyceryl-6 distearate, jojoba esters, polyglyceryl-6 polyricinoleate, phenoxyethanol, *Citrullus lanatus* (watermelon) fruit extract, sodium acrylates copolymer, chlorphenesin, sodium PCA, lens esculenta (lentil) seed extract, beeswax, cetyl alcohol, acrylates/C10-30 alkyl acrylate crosspolymer, xanthan gum, *Pyrus malus* (apple) fruit extract, lecithin, ethylhexylglycerin, tetrasodium glutamate diacetate, sodium lactate, aminomethyl propanol, hydroxypropyl methylcellulose stearoxy ether, propanediol, sodium acetylated hyaluronate, sodium hyaluronate, potassium sorbate, sodium benzoate, pancratium maritimum extract, sodium hydroxide).

The study was a single-blind, split-face, randomized, clinical study with 25 subjects, each a healthy female volunteer, between the ages of 25 and 40 years, Fitzpatrick Type I-III. The following test articles were supplied by the Sponsor:
1. Device: AgeLOC LumiSpa Microcurrent Attachment with PRPWM—Investigational;
2. Topical: Nu Skin Conductive Gel; and
3. Topical: MC Boost "East".

Treatment procedure for Conductive Gel topical was as follows:
1. Study Staff applied, with a gloved finger/hand, a dime-sized amount of product to one approximately 2-inch (about 5.08 cm) diameter circle defined on one of the subject's cheeks (randomized as to the topical applied.)
2. Study staff took no more than 10 seconds to apply the product to the cheek.
3. After product application, study staff immediately turned on the Age LOC LumiSpa Microcurrent Attachment device with PRPWM and conducted a 20 second treatment on the subjects' cheek treatment area, being sure to stay within a drawn circle for product application.
4. Laser Doppler and Temperature readings were taken at the center of the 2-inch (5.08 cm) diameter circle no more than 2 minutes post-treatment with PRPWM.

Treatment procedure for MC Boost "East" topical: Study staff repeated steps 1-4 above on the subject's other cheek.

On study day 1 (baseline), subjects attended the test facility with a clean face, free of makeup. Prior to acceptance on the study, subjects provided written informed consent and were screened for study eligibility. Subjects were queried as to their medical history and any concomitant medications. Skin condition on the face was assessed and demographic information was collected.

Subjects acclimated for a minimum of 30 minutes to indoor temperatures prior to instrumental assessments. Subjects had an approximately 2-inch (about 5.08 cm) diameter circle test site drawn on each side of their face by the investigator or designee prior to instrumental assessments. Subjects had baseline temperature readings and Laser Doppler instrumental assessments on both sides of the face within the test sites. Subjects had the application of test products and PRPWM device use conducted by the investigator or designee (see treatment procedure above). The side of the face treated with the Conductive Gel was randomized to the right or left side of the face. Following the treatment to each side of the face, the subjects repeated the same instrumental assessments on both sides of the face.

The instrumental and visual assessments included:
Laser Doppler flowmetry—A Laser Doppler Imager (Moor LD12-IR) was used to measure cutaneous blood flow (mean flux–arbitrary units). The LD12-IR system used a 785 nm near-IR laser (maximum power 2.5 mW) for the measurement. The maximum penetration depth is between 2-3 mm of the skin. The area to be measured was approximately 1-inch diameter (about 2.54 cm), centered on the approximately 2-inch (about 5.08 in) diameter treatment area. Subjects were asked to remain as still as possible while laser Doppler readings were taken. Subject's eyes were covered so that their eye area was not exposed to the laser. One measurement was taken on each side of the face at baseline (prior to treatment), and post-treatment.

Temperature assessments—Temperature assessments were taken with a non-contact infrared device (Equinox International EQ-THERM03) at baseline and post-treatment on the skin surface within the 2-inch (5.08 cm) diameter treatment area on each cheek.

Visual assessment—Subject's overall skin condition was assessed to ensure qualification for the study.

Statistical Analysis. The source data were the laser Doppler and temperature assessments at each time interval (baseline, 2 minutes post-treatment). Within-treatment analyses were conducted on changes from baseline, utilizing t-tests. Between-treatment analyses were conducted on change from baseline utilizing analysis of variance with the baseline value as the covariate. All statistical tests of the hypothesis were two sided and employed a level of significance of 0.05 and no adjustment was made for the number of tests performed.

Figures 15A, 15B:
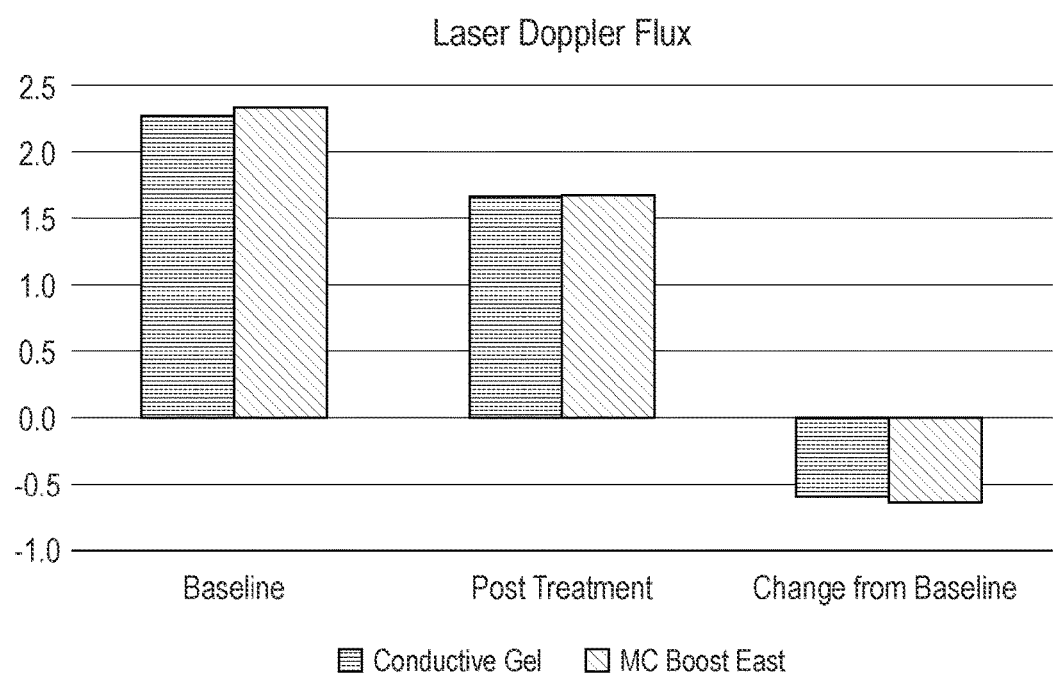
FIGS. 15A and 15B are a table and bar chart, respectively, summarizing laser Doppler flux measurement data according to exemplary applications of a device for generating and applying modulated waveform stimuli, as described herein.

FIGS. 15A and 15B are a table and bar chart, respectively, summarizing data from the laser Doppler assessments. In the bar chart of FIG. 15B, there are three pairs of bar graphs. The left-hand bar in each pair shows data for the conductive gel (from Example 1), and the right-hand bar in each pair shows data from the MC Boost "East" gel (described above).

Figures 16A, 16B:
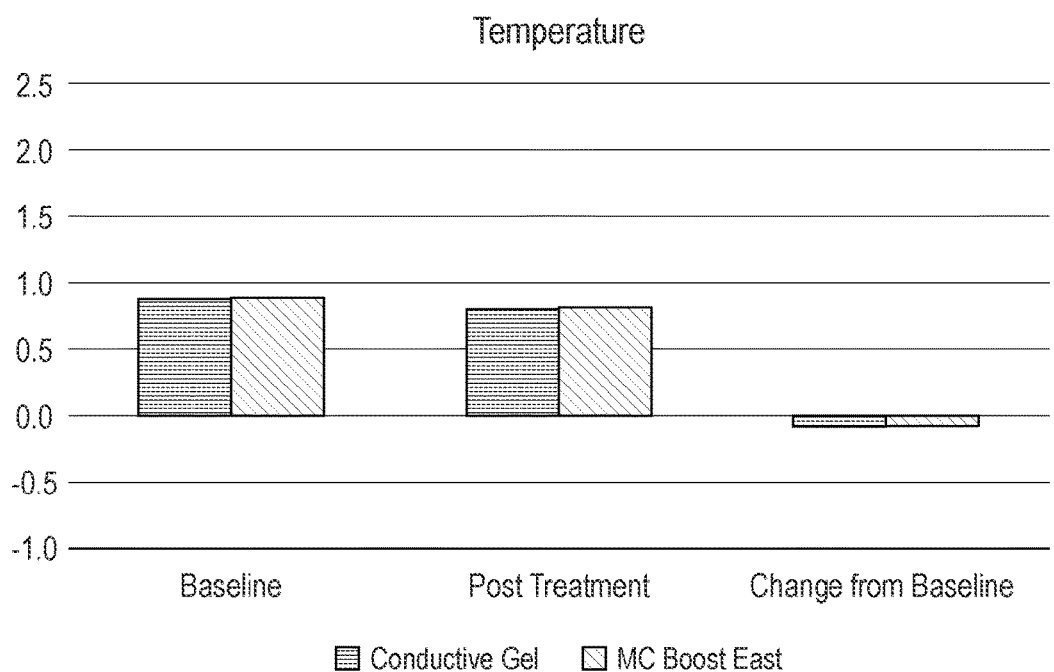
FIGS. 16A and 16B are table and bar chart, respectively, summarizing temperature measurement data for the representative applications illustrated in FIGS. 15A and 15B.

FIGS. 16A and 16B are a table and bar chart, respectively, summarizing the data from the temperature assessments. Again, the left-hand bar in each pair shows data from the conductive gel (from Example 1), while the orange or right-hand bar in each pair shows data from the MC Boost "East" gel (described above).

Study conclusions: Between-treatment and within-treatment analyses were conducted on changes from baseline for mean flux (blood flow) and facial temperature assessments. Within-treatment analyses showed a statistically significant decrease from baseline for both mean flux and temperature for both treated sites. There were no statistically significant differences between treatments for either mean flux or temperature. While not being bound by theory, it is believed that the decreases may have been caused by vasoconstriction, but the mechanisms for vasoconstriction in the circumstances of the experiment are not currently completely understood.

EXAMPLE 3: Male subjects tolerability study. An important aspect of microcurrent treatment of facial skin is tolerability. Treatment with microcurrent is typically not acceptable if it is substantially uncomfortable or painful, or, for some persons, producing even mild discomfort. To study tolerability of a microcurrent attachment with PRPWM this study was performed with a sample of male subjects, in connection with shaving.

It is known that freshly shaved skin typically is more sensitive than other skin. Six male participants between ages 25-40 completed a comparative evaluation using a microcurrent attachment with PRPWM and also using a Nu Skin ageLOC Galvanic Spa. The latter provides low levels of direct current to the skin. While conductive conditions and sensitivity vary from person to person, and on any applied lotion or other material, a Nu Skin ageLOC Galvanic Spa typically provides current two and a half times lower than the current needed to produce only a slight sensation.

Participants in the tolerability study shaved with their own shave cream/gel/topical and razor and were provided with a microcurrent attachment with PRPWM and also a Nu Skin ageLOC Galvanic Spa. Immediately post-shave, participants used the ageLOC Galvanic Spa on setting 1 on one side of their face (cheek area). An observing clinical investigator noted how long the subject was able to tolerate the device comfortably. Participants then used the ageLOC Galvanic Spa on setting 2 on the same side of their face (cheek area). Again, the observing clinical investigator noted how long the subject was able to tolerate the device comfortably. After use of the ageLOC Galvanic Spa on settings 1 and 2, participants used the ageLOC LumiSpa Microcurrent Attachment device with PRPWM on the other side of their face. Again, the observing clinical investigator noted how long the subject was able to tolerate the device comfortably.

FIG. 17 is a table summarizing data from the male subject tolerability study in Example 3. The table in FIG. 17 shows the results observed by the clinical investigator for the three different current treatments described in the preceding. It should be noted that ageLOC Galvanic Spa on setting 1 is a positive polarity microcurrent, and the current can self-set to 0.125 mA, 0.250 mA, or 0.350 mA (±10%). The self-setting is based on the capacitance of the skin in the area touched, the environmental conditions at the time and the physiological conditions of the subject's skin at the time of application.

When ageLOC Galvanic Spa is on setting 2 there is a negative polarity microcurrent, and the current can self-set to the same levels as for setting 1. Setting 1 has a duration of 2 minutes and setting 2 has a duration of 3 minutes, but the user can remove the device from the skin at any time. Some users shortened treatment, as shown in the table.

The results in Example 3 showed that by comparison to treatment with the two settings (1 and 2) of the ageLOC Galvanic Spa, the ageLOC LumiSpa Microcurrent Attachment device with PRPWM was more tolerable; i.e., it was perceived as more gentle on freshly shaved skin. Specifically, the PRPWM microcurrent treatment device was tolerable without discomfort for a 30 second treatment cycle, while the ageLOC Galvanic Spa on setting 1 could be tolerated for between one and three seconds by the subjects using setting 1. For ageLOC Galvanic Spa on setting 2, one subject tolerated up to 25 seconds, and the remainder tolerated 1 to 6 seconds.

Representative Applications, Examples and Embodiments

Representative device applications, examples and embodiments include one or more emitters configured for application of a stimulus to a skin surface of a subject, a voltage source or current supply, and a computer-based controller. The voltage source or current supply can be adapted to generate a waveform for application of the stimulus to the skin surface of the subject, via the one or more emitters. The controller can be configured with memory and processor hardware adapted for modulating a set of consecutive pulses in the waveform.

In any of these applications, examples and embodiments, the set of consecutive pulses can define a treatment cycle having one or more phases; e.g., with each of the phases defining a continuous subset of the consecutive pulses. The pulse widths or absolute integrated amplitudes (or other amplitude) of the consecutive pulses in each of the phases can vary in at least one continuous subset defining at least one of the phases, or in each of the subsets defining each of the phases, or over the set of consecutive pulses defining the treatment cycle, either alternatively or in combination. For example, the pulse widths or absolute integrated amplitudes may be non-repeating or aperiodic over one or more of the phases in the treatment cycle, or over each of the phases in the treatment cycle, or they may otherwise vary over one or more of the phases in the treatment cycle, or over each of the phases in the treatment cycle.

In any of these applications, examples and embodiments, the pulse widths or absolute integrated amplitudes (or other amplitude) of the consecutive pulses may vary in a predefined, randomized or pseudorandom sequence, so that the pulse widths or absolute integrated amplitudes are non-repeating in one or more of the phases, in each of the phases, or over the set of consecutive pulses defining the treatment cycle, alternatively or in any combination. The predefined, randomized or pseudorandom sequence may also be shifted or reordered between phases, or otherwise constrained to provide a same duty cycle over each phase, or to provide charge balance over two or more of the phases having consecutive pulses of opposite polarity, or both. The sequence can be shifted or reordered between phases, so that the pulse widths or absolute integrated amplitudes vary in a different sequence in two or more of the phases.

In any of these applications, examples and embodiments, the pulse widths and absolute integrated amplitudes (or other amplitude) of the consecutive pulses can be determined at least in part based on a random or pseudorandom number generator. The pulse widths and absolute integrated amplitudes of consecutive pulses can also comprise or include a random, predetermined, or pseudorandom component, so that the absolute integrated amplitudes of the consecutive pulses has a same absolute value over each subset of the consecutive pulses, defining two or more of the phases, or over each of the phases.

In any of these applications, examples and embodiments, the pulse width, period, frequency, or absolute integrated amplitude (or other amplitude) of the consecutive pulses may vary, in any combination. The variation can be aperiodic or non-repeating, so that the modulated parameter does not repeat at all, or does not repeat with any identifiable pattern or sequence, over a given set of pulses defining a treatment cycle, or over a subset of consecutive pulses defining a phase of the treatment cycle, or both.

In any of these applications, examples and embodiments, the variation in the modulated pulse parameter can be at least 1% or at least 10% of the nominal or average value of the parameter, or less, where the nominal or average value is determined across a subset of consecutive pulses defining a phase of a selected treatment cycle, or across the set of consecutive pulses defining the treatment cycle. The variation in the modulated pulse parameter can also be at least 20% of the nominal or average value, for example up to 50% of the nominal or average value, or up to 100% of or up to two times the nominal or average value, in any order or combination with the lower limits of at least 1% or at least 10% of the nominal or average value of the parameter. The variation in the modulated pulse parameter can also extend up to ten times the nominal or average value, or up to one hundred times the nominal or average value, or more, in any order or combination with the other limits.

In any of these applications, examples and embodiments, the one or more phases can comprise a first phase (or one or more first phases) having a first continuous subset of the consecutive pulses with a first polarity and a second phase (or one or more second phases) having a second continuous subset of the consecutive pulses with a second polarity, opposite the first polarity. The absolute integrated amplitudes (or other amplitude) of the consecutive pulses can vary, so that the amplitudes are non-repeating or aperiodic across the subset of consecutive pulses defining each of the phases, or both, exclusively or inclusively, or non-repeating or aperiodic across the set of consecutive pulses defining the treatment cycle, or both, exclusively or inclusively.

In any of these applications, examples and embodiments, the subset of consecutive pulses in each phase can have a constant absolute integrated amplitude, or other constant amplitude. A period of the subset of consecutive pulses can be fixed, such that a frequency of the consecutive pulses is constant across one or more of the phases, or over each of the phases in the treatment cycle, or over the set of consecutive pulses defining the treatment cycle.

In any of these applications, examples and embodiments, a frequency of the subset of consecutive pulses in each phase can vary, so that a period of the consecutive pulses is non-repeating or aperiodic across one or more of the phases, or over each of the phases in the treatment cycle, or over the set of consecutive pulses defining the treatment cycle.

In any of these applications, examples and embodiments, each of the consecutive pulses can comprises a first segment having a first absolute integrated amplitude (or other amplitude); e.g., with a second segment having a second amplitude or no amplitude, where the first and second segments have a same width. Each of the consecutive pulses can comprise first and second segments with different widths.

In any of these applications, examples and embodiments, the one or more emitters can comprise at least one electrode disposed adjacent the skin surface. The waveform can comprise an electrical waveform adapted for application of the stimulus to the skin surface as a microcurrent treatment, emitted via the at least one electrode. The modulated waveform can be adapted to apply the microcurrent treatment directly to the skin surface, or through a conductive fluid disposed on the skin surface, or between the skin surface and the at least one electrode. A sensor can be configured to generate feedback responsive to propagation of the stimulus into or through the skin surface of the subject, for example with a sensor circuit couple to one of the emitters or using a separate sensor device, where the waveform is modulated based on the feedback to apply the microcurrent treatment to the skin surface through a fluid disposed on the skin surface, or between the skin surface and the at least one electrode.

Representative method applications, examples and embodiments include modulating a waveform for application of a stimulus to a skin surface of a subject. Suitable methods can include providing a device adjacent the skin surface of the subject, supplying a voltage or current adapted to generate a waveform for application of the stimulus to the skin surface, and modulating a set of consecutive pulses in the waveform; e.g., using one or more emitters configured for administering the stimulus to the skin surface.

In any of these applications, examples and embodiments, the set of consecutive pulses can define a treatment cycle having one or more phases; e.g., with each of the phases defining a continuous subset of the consecutive pulses. The pulse widths or absolute integrated amplitudes of the consecutive pulses can vary over at least one continuous subset defining at least one phase, or over the set of consecutive pulses defining the treatment cycle (e.g., across each of the subsets defining each of the phases). For example, the pulse widths or absolute integrated amplitudes may be non-repeating or aperiodic over the one or more of the phases, or over one or more of the continuous subsets of consecutive pulses defining each phase, or over the full set of consecutive pulses defining the treatment cycle, exclusively or in combination.

In any of these applications, examples and embodiments, the pulse widths or absolute integrated amplitudes (or other amplitude) of the consecutive pulses can vary in a predefined, randomized or pseudorandom sequence, so that the pulse widths or amplitudes are non-repeating or aperiodic over one or more of the phases, or over each of the phases, or over the set of consecutive pulses defining the treatment cycle. The sequence can be shifted or reordered between phases, so that the pulse widths or absolute integrated amplitudes (or other amplitudes) vary differently in the subsets of consecutive pulses defining two or more of the phases; e.g., varying in a difference sequence in two or more phases. The sequence can constrained to provide a same duty cycle over each phase, or over two or more phases, or to provide charge balance over two or more of the phases having consecutive pulses with opposite polarity, or both, exclusively or in combination.

In any of these applications, examples and embodiments, the absolute integrated amplitudes (or other amplitude) of the subset of consecutive pulses in each phase can vary, so that the amplitude is aperiodic or non-repeating across one or more of the phases, or over each of the phases, or across the subset of consecutive pulses defining each of the phases, or across the set of consecutive pulses defining the treatment cycle, exclusively or in any combination. A frequency of the subset of consecutive pulses in each phase can vary, so that a period of the consecutive pulses is non-repeating or aperiodic across each phase, or across the set of consecutive pulses defining the treatment cycle, exclusively or in combination.

A non-transitory, machine readable data storage medium can be provided with program code stored thereon. The program code can be executable by a microprocessor or other computing device, in order to operate a device or perform a method according to any of these applications, examples and embodiments.

Representative skin treatment system applications, examples and embodiments can also include one or more emitters configured for emitting a stimulus for application to a skin surface of a subject, a voltage source or current supply configured to generate a waveform for application of the stimulus to the skin surface, via the one or more emitters, and a controller configured for modulating a set of consecutive pulses in the waveform. The set of consecutive pulses can define a treatment cycle having one or more phases; e.g., with each of the phases defining a continuous subset of the consecutive pulses. The consecutive pulses can vary by pulse width, period, frequency or amplitude; e.g., in a random, pseudorandom, or preselected sequence, so that the consecutive pulses are non-repeating or aperiodic over the subset of consecutive pulses defining one or more of the phases, or over each of the phases, or over the set of consecutive pulses defining the treatment cycle, either exclusively or in combination.

In any of these applications, examples and embodiments, the one or more emitters can comprise one or more electrodes configured to emit the stimulus as an energetic voltage or current stimulus applied to the skin surface. The one or more emitters can comprise one or more transducers configured to generate the stimulus as an energetic subsonic, sonic, ultrasonic, or acoustic stimulus applied to the skin surface. The one or more emitters can comprise one or more LEDs, lasers, or other electromagnetic sources configured to generate the stimulus as an energetic radio frequency (RF), infrared (IR), near-ultraviolet (near-UV) or ultraviolet (UV) stimulus. The one or more emitters can comprise any combination of such electrodes, transducers, LEDs, lasers, or other electromagnetic sources.

In any of these applications, examples and embodiments, the consecutive pulses can vary in a predefined, randomized or pseudorandom sequence, so that the consecutive pulses are non-repeating or aperiodic over at least one of the phases, or over each of the phases, or over the consecutive set of pulses defining the treatment cycle. The sequence can be constrained to provide a same duty cycle over each phase, or to provide charge balance over two or more of the phases having consecutive pulses with opposite polarity. The sequence can be shifted or reordered (e.g., between phases), so that the subsets of consecutive pulses provide a same duty cycle over each phase, or provide charge balance over two or more phases having consecutive pulses with opposite polarity.

In any of these applications, examples and embodiments, the waveform can be further modulated based on feedback responsive to propagation of the stimulus from the one or more emitters into or through the skin surface of the subject; e.g., via a topical agent applied between the emitters and the skin surface, or with a fluid (e.g., a conducting fluid) disposed between the emitters and the skin surface, or without such a topical agent or fluid.

A non-transitory, machine readable data storage medium can be provided with program code stored thereon; e.g., where the program code is executable by a microprocessor to operate a portable computing device, such as a smart phone, tablet, personal computer, or other user computing device. The portable computing device can be configured in communication with a device according to any of these applications, examples and embodiments; e.g., where the one or more emitters are configured for emitting the stimulus, the voltage or current supply is configured to generate the waveform, the controller is configured for modulating the set of consecutive pulses in the waveform, or the consecutive pulses are varied by pulse width, period, frequency or amplitude, by operation of the portable computing device.

In any of these applications, examples and embodiments, the device can include an interface (e.g., a wired or wireless interface) configured for communication with a portable computing device having a non-transitory, machine readable data storage medium with program code stored thereon, the program code executable by a microprocessor to operate the portable computing device in communication with the skin treatment device, where the stimulus can be selected by operation of the portable computing device, or where the portable computing device can be configured to select the stimulus. Suitable portable computing devices include, but are not limited to, mobile phones, tablet computers, smart phones, smart watches, personal computers, and other personal computing devices.

Combinations, Modifications and Equivalents

This disclosure has been made with respect to representative examples and embodiments. Each and every example embodiment of the invention disclosed here can be used either alone or in combination with any other embodiment or example that is described or illustrated herein, and each may incorporate additional modifications, changes, equivalents, and alternatives that fall within the breadth of disclosure, as read and understood by a person of ordinary skill, and without departing from practice of the invention as claimed. These various examples and embodiments are provided by way of illustration, and should not be construed to limit the scope of the invention, nor to limit the meets and bounds of coverage as defined by the plain language of the claims.

The invention claimed is:

1. A device comprising:
   one or more emitters configured for application of a stimulus to a skin surface of a subject;
   a voltage or current supply adapted to generate a waveform for application of the stimulus to the skin surface of the subject, via the one or more emitters; and
   a controller configured to, during a treatment cycle, modulate a first set of consecutive pulses during a first phase of the waveform and to modulate a second set of consecutive pulses during a second phase of the waveform;
   wherein respective pulse widths or absolute integrated amplitudes of pulses of the first set of consecutive pulses vary in a first predefined, randomized or pseudorandom sequence, such that the respective pulse widths or absolute integrated amplitudes are non-repeating or aperiodic;
   wherein respective pulse widths or absolute integrated amplitudes of pulses of the second set of consecutive pulses vary in a second predefined, randomized or pseudorandom sequence, such that the respective pulse widths or absolute integrated amplitudes are non-repeating or aperiodic; and
   wherein the pulses of the first set of consecutive pulses have a first polarity and the pulses of the second set of consecutive pulses have a second polarity opposite the first polarity, wherein, collectively, the first set of consecutive pulses and the second set of consecutive pulses are constrained to provide charge balance across the first and second phases.

2. The device of claim 1, wherein the first sequence and the second sequence have a common duty cycle between the first phase and the second phase.

3. The device of claim 1, wherein the pulse widths or the absolute integrated amplitudes vary in different sequences in the first phase and the second phase.

4. The device of claim 1, wherein the pulse widths and the absolute integrated amplitudes of the first set of consecutive pulses and second set of consecutive pulses are determined at least in part based on a random or pseudorandom number generator, or wherein the pulse widths and the absolute integrated amplitudes of the first set of consecutive pulses and second set of consecutive pulses each comprise a random, predetermined, or pseudorandom component.

5. The device of claim 1, wherein the absolute integrated amplitude of the first set of consecutive pulses and second set of consecutive pulses varies, such that the absolute integrated amplitude is non-repeating across the first and second phases, or aperiodic across the first and second set of consecutive pulses defining the treatment cycle.

6. The device of claim 1, wherein the first set of consecutive pulses in the first phase has a constant absolute integrated amplitude.

7. The device of claim 1, wherein an instantaneous carrier frequency f of the first set of consecutive pulses and of the second set of consecutive pulses varies from pulse to pulse, such that a pulse-to-pulse period T of the first and second sets of consecutive pulses is non-repeating or aperiodic, wherein the instantaneous carrier frequency $f=1/T$.

8. The device of claim 1, wherein each of the first and second sets of consecutive pulses comprises a first segment having a first amplitude and further comprising a second segment having a second amplitude or no amplitude, wherein the first and second segments have different widths.

9. The device of claim 1, wherein the one or more emitters comprise at least one electrode disposed adjacent the skin surface, and wherein the waveform comprises an electrical waveform adapted for application of the stimulus to the skin surface as a microcurrent treatment, emitted via the at least one electrode.

10. The device of claim 9, further comprising a sensor configured to generate feedback responsive to propagation of the stimulus into or through the skin surface of the subject, wherein the waveform is modulated based on the feedback to apply the microcurrent treatment to the skin surface through a fluid disposed on the skin surface, or between the skin surface and the at least one electrode.

11. The device of claim 1, wherein the absolute integrated amplitudes of the first and second sets of consecutive pulses have a same total integrated pulse amplitude.

12. The device of claim 1, wherein a pulse-to-pulse period T0 of the first set of consecutive pulses and the second set of consecutive pulses is fixed, such that a carrier frequency f=1/T0 of the first set of consecutive pulses and second set of consecutive pulses is constant.

13. A method for modulating a waveform for application of a stimulus to a skin surface of a subject, the method comprising:
    providing a device adjacent the skin surface of the subject, the device comprising one or more emitters configured for administering the stimulus to the skin surface;
    supplying a voltage or current adapted to generate a waveform for application of the stimulus to the skin surface, via the one or more emitters; and
    modulating a first set of consecutive pulses during a first phase of the waveform, wherein the first set of consecutive pulses defines a first phase of a treatment cycle;
    modulating a second set of consecutive pulses during a second phase of the waveform, wherein the second set of consecutive pulses defines a second phase of the treatment cycle;
    wherein respective pulse widths or absolute integrated amplitudes of the first set of consecutive pulses vary in a first predefined, randomized or pseudorandom sequence, such that the respective pulse widths or absolute integrated amplitudes are non-repeating or aperiodic over the first phase;
    wherein respective pulse widths or absolute integrated amplitudes of the second set of consecutive pulses vary in a second predefined, randomized or pseudorandom sequence, such that the respective pulse widths or absolute integrated amplitudes are non-repeating or aperiodic over the second phase; and
    wherein the pulses of the first set of consecutive pulses have a first polarity and the pulses of the second set of consecutive pulses have a second polarity opposite the first polarity, wherein, collectively, the first set of consecutive pulses and the second set of consecutive pulses are constrained to provide charge balance across the first and second phases.

14. The method of claim 13, further comprising shifting or reordering the second sequence, such that the pulse widths or the absolute integrated amplitudes vary in a different sequence between the first phase and the second phase.

15. The method of claim 13, wherein the first sequence and the second sequence have a common duty cycle over the first phase and the second phase.

16. The method of claim 13, wherein the absolute integrated amplitudes of the first set of consecutive pulses and the second set of consecutive pulses vary from pulse to pulse, such that the absolute integrated amplitudes are aperiodic or non-repeating.

17. The method of claim 13, wherein an instantaneous carrier frequency f of the first set of consecutive pulses and of the second set of consecutive pulses varies from pulse to pulse, such that a pulse-to-pulse period T of the first and second set of consecutive pulses is non-repeating or aperiodic, wherein the instantaneous carrier frequency f=1/T.

18. A non-transitory, machine readable data storage medium with program code stored thereon, the program code executable by a microprocessor to operate a device according to the method of claim 13.

19. A skin treatment system comprising:
    one or more emitters configured for emitting a stimulus for application to a skin surface of a subject;
    a voltage or current supply adapted to generate a waveform adapted for application of the stimulus to the skin surface, via the one or more emitters; and
    a controller configured for modulating, during a treatment cycle, a first set of consecutive pulses during a first phase of the waveform and a second set of consecutive pulses during a second phase of the waveform;
    wherein respective pulses of the first set of consecutive pulses vary by pulse width, period, frequency or absolute amplitude, in a first random, pseudorandom, or preselected sequence, such that the first set of consecutive pulses are non-repeating or aperiodic;
    wherein respective pulses of the second set of consecutive pulses vary by pulse width, period, frequency or absolute amplitude, in a second random, pseudorandom, or preselected sequence, such that the second set of consecutive pulses are non-repeating or aperiodic; and
    wherein the pulses of the first set of consecutive pulses have a first polarity and the pulses of the second set of consecutive pulses have a second polarity opposite the first polarity, wherein the first set of consecutive pulses and the second set of consecutive pulses are constrained to provide charge balance across the first and second phases.

20. The system of claim 19, wherein the one or more emitters comprise:
    one or more electrodes configured to emit the stimulus as an energetic voltage or current stimulus applied to the skin surface; or
    one or more transducers configured to generate the stimulus as an energetic subsonic, sonic, ultrasonic, or acoustic stimulus applied to the skin surface; or
    one or more LEDs, lasers, or other electromagnetic sources configured to generate the stimulus as an energetic radio frequency (RF), infrared (IR), near-ultraviolet (near-UV) or ultraviolet (UV) stimulus; or any combination thereof.

21. The system of claim 20, wherein the first sequence and the second sequence have a common duty cycle over each phase.

22. The system of claim 19, wherein the pulse widths of the first set of consecutive pulses and the second set of consecutive pulses are non-repeating or aperiodic over the treatment cycle.

23. The system of claim 19, wherein the waveform is further modulated based on feedback responsive to propagation of the stimulus from the one or more emitters into or through the skin surface of the subject via a topical agent applied between the emitters and the skin surface.

24. The system of claim 19, further comprising an interface configured for communication with a portable computing device having a non-transitory, machine readable data storage medium with program code stored thereon, the program code executable by a microprocessor to operate the portable computing device in communication with the skin treatment device, wherein the portable computing device is configured for selecting the stimulus, modulating the waveform, or exchanging user data with the skin treatment system.

25. The system of claim 19, wherein the first and second sequences are the same.

26. The system of claim 19, wherein the first and second sequences are different, such that the pulse widths or the absolute amplitudes vary in different sequences in the first phase and the second phase.

27. The system of claim 19, wherein the first and second sequences are different, such that the pulse widths or the absolute amplitudes vary in different sequences in two or more instances of said first and second phases.

* * * * *